US006613921B2

(12) United States Patent
Campbell, Jr. et al.

(10) Patent No.: US 6,613,921 B2
(45) Date of Patent: Sep. 2, 2003

(54) POLYCYCLIC, FUSED RING COMPOUNDS, METAL COMPLEXES AND POLYMERIZATION PROCESS

(75) Inventors: Richard E. Campbell, Jr., Midland, MI (US); Jerzy Klosin, Midland, MI (US); Ravi B. Shankar, Midland, MI (US); Francis J. Timmers, Midland, MI (US); Robert K. Rosen, Houston, TX (US)

(73) Assignee: Dow Global Technologies Inc., Midland, MI (US)

( * ) Notice: Subject to any disclaimer, the term of this patent is extended or adjusted under 35 U.S.C. 154(b) by 121 days.

(21) Appl. No.: 09/879,463

(22) Filed: Jun. 12, 2001

(65) Prior Publication Data

US 2002/0062011 A1 May 23, 2002

Related U.S. Application Data

(60) Provisional application No. 60/215,456, filed on Jun. 30, 2000.

(51) Int. Cl.$^7$ .......................... C07F 17/00; B01J 31/00; C08F 4/44
(52) U.S. Cl. .................. 556/7; 556/11; 556/12; 556/20; 556/23; 556/28; 556/43; 556/46; 556/53; 556/58; 556/136; 556/140; 534/15; 585/506; 502/103; 502/117; 526/160; 526/943
(58) Field of Search .................... 556/7, 11, 12, 556/20, 23, 28, 43, 46, 53, 58, 136, 140; 534/15; 502/103, 117; 526/160, 943; 585/506

(56) References Cited

U.S. PATENT DOCUMENTS

| | | | |
|---|---|---|---|
| 3,310,656 A | 3/1967 | Galantay | 260/288 |
| 5,321,106 A | 6/1994 | LaPointe | 526/126 |
| 5,374,696 A | 12/1994 | Rosen et al. | 526/126 |
| 5,470,993 A | 11/1995 | Devore et al. | 556/11 |
| 5,486,632 A | 1/1996 | Devore et al. | 556/11 |
| 5,489,659 A | 2/1996 | Sugano et al. | 526/127 |
| 5,510,502 A | 4/1996 | Sugano et al. | 556/11 |
| 5,541,349 A | 7/1996 | Wilson et al. | 556/10 |
| 5,561,093 A | 10/1996 | Fujita et al. | 502/117 |
| 5,594,081 A | 1/1997 | Uchino et al. | 526/127 |
| 5,703,187 A | 12/1997 | Timmers | 526/282 |
| 5,721,185 A | 2/1998 | LaPointe et al. | 502/117 |

FOREIGN PATENT DOCUMENTS

| | | |
|---|---|---|
| EP | 697418 B1 | 2/1996 |
| EP | 0 846 696 A1 | 6/1998 |
| EP | 0 849 273 A1 | 6/1998 |
| EP | 0 945 458 A2 | 9/1999 |
| EP | 0 963 996 A2 | 12/1999 |
| EP | 0 985 674 A1 | 3/2000 |
| WO | WO 97/15583 | 5/1997 |
| WO | WO 97/19463 | 5/1997 |
| WO | WO 99/02540 | 1/1999 |
| WO | WO 99/14221 | 3/1999 |
| WO | WO 00/63178 | 4/1999 |

OTHER PUBLICATIONS

Chemical Abstracts, Sasaki, Hideaki et al., "Synthesis of '3n!cyclophanes and related compounds by alkylation of tosylmethyl isocyanide with bis(bromomethyl) benzenes", (1983), 31(8), p. 2868–2878.
Justus Liebigns Ann. Chem. Reid, Walter et al., "Reactions with cyclopentadienones. XXIX. Assignment of geminal coupling constants in the 1H–NMR spectrum of a dihydroazulene using deuterated compounds", (1974) (2), 201–205, and p. 1239–1247.
Chemische Berichte, Hafelinger et al., "Spektroskopische Effekte von Phenylsubstituion am Benzyl–Anion", (1968), (101), p. 672–680.
Journal of the American Chemical Society, Lansbury et al., "Intramolecular 1,3—Proton Transfers during Isofluronene-Fluorene Isomerizati0n", (1968), (90), p. 6544–6546.
Journal of Chemical Society, Campbell et al., "Synthesis of 2:3–Benzofluoranthene", (1951), p. 2941–2943.
Journal of Organic Chemistry, Streitweiser et al., "Carbon Acidity. 55.", (1978), (43), p.598–600.
Bulletin of Chemical Society of Japan, Oki et al., Reactivites of Stable Rotamers, (1999) (72), p 63–72.

Primary Examiner—Porfirio Nazario-Gonzalez

(57) ABSTRACT

Compounds and metal complexes comprising a polycyclic, fused ring ligand or inertly substituted derivative thereof having up to 60 atoms other than hydrogen, said ligand comprising at least: (1) a cyclopentadienyl ring, (2) a 6, 7, or 8 membered ring other than a 6-carbon aromatic ring, and (3) an aromatic ring, with the proviso that said 6, 7, or 8 membered ring (2), is fused to both the cyclopentadienyl ring (1), and the aromatic ring (3), polymerization catalysts, a process to prepare the novel compounds and complexes, and olefin polymerization processes using the same are disclosed.

6 Claims, No Drawings

US 6,613,921 B2

POLYCYCLIC, FUSED RING COMPOUNDS, METAL COMPLEXES AND POLYMERIZATION PROCESS

CROSS REFERENCE STATEMENT

This application claims the benefit of U.S. Provisional Application No. 60/215,456, filed Jun. 30, 2000.

BACKGROUND OF THE INVENTION

This invention relates to a class of polycyclic, fused ring compounds, metal complexes formed therefrom, and to polymerization catalysts derived from such complexes that are particularly suitable for use in a polymerization process for preparing homopolymers and copolymers of olefins or diolefins, including copolymers comprising two or more olefins or diolefins such as copolymers comprising a monovinyl aromatic monomer and ethylene.

Constrained geometry metal complexes and methods for their preparation are disclosed in U.S. Pat. No. 5,703,187. This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. Pat. Nos. 5,321,106, 5,721,185, 5,374,696, 5,470,993, 5,541,349, and 5,486,632, as well as WO97/15583, and WO97/19463.

Certain highly active, polyaromatic, metal complexes, especially derivatives of cyclopentaphenanthrenyl ligand groups are disclosed in U.S. Ser. No. 09/122,958, filed Jul. 27, 1998, (WO99/14221, published Mar. 25, 1999). Despite the advance in the art occasioned by the foregoing cyclopentaphenanthrenyl containing metal complexes, it would be desirable to provide improved metal complexes that do not contain fused, polycyclic aromatic hydrocarbon functionality, in as much as the same may be associated with potentially adverse biological activity. Accordingly, it would be desirable if there were provided metal complexes having similar or improved catalytic properties to the foregoing cyclopentaphenanthrenyl derivatives and also having improved biological properties. Metallocenes containing four fused rings arranged on a central 5-membered carbon ring are disclosed in WO99/02540.

SUMMARY OF THE INVENTION

According to the present invention there is provided a polycyclic, fused ring compound corresponding to the formula: $(Cp^*)_p\text{-}M^*$ (I) or $CpM(Z)_z(X)_x(L)_l(X')_{x'}$ (II), where $Cp^*$ is a polycyclic, fused ring ligand or inertly substituted derivative thereof comprising at least: (1) a cyclopentadienyl ring, (2) a 6,7,or 8 membered ring other than a 6-carbon aromatic ring, and (3) an aromatic ring, with the proviso that said 6, 7, or 8 membered ring (2), is fused to both the cyclopentadienyl ring (1), and the aromatic ring (3), said $Cp^*$ having up to 60 atoms other than hydrogen;

p is 1 or 2;

when p is 1, M* is hydrogen, an alkali metal or an alkaline earth metal halide, and, when p is 2, M* is an alkaline earth metal; said M* being bound to at least one of the non-fused, ring-carbons of the cyclopentadienyl ring, (1);

Cp is the aromatic ligand group derived from Cp* by removal of M*;

M is a metal selected from Groups 3–10 or the Lanthanide series of the Periodic Table of the Elements;

Z is either:

a) a cyclic ligand group containing delocalized π-electrons, including a second or third, fused, polycyclic ligand, Cp, said Z being bonded to M by means of delocalized π-electrons and optionally also covalently bonded to Cp through a divalent bridging group, Z', or b) a divalent moiety of the formula -Z'Y—, wherein,
Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;

Y is —O—, —S—, —$NR^5$-, —$PR^5$-; —$NR^5_2$, or —$PR^5_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;

L'' is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;

z is 0, 1 or 2;

x is 0, 1, 2, or 3;

l is a number from 0 to 2, and x' is 0 or 1.

The above compounds may exist as isolated crystals, as a mixture with other compounds, in the form of a solvated adduct, dissolved in a solvent, especially an organic liquid solvent, in the form of a dimer, or as a chelated derivative, especially wherein the chelating agent is an organic material such as ethylenediaminetetraacetic acid (EDTA).

A further embodiment of the present invention includes a process for forming a cyclopentenone from a halogenated cyclic olefin by forming a trihydrocarbyl-substituted acetylenic derivative thereof and thereafter carbonylating and ring closing the same to form the desired cyclopentenone product. The cyclopentenone may be readily reduced and dehydrated to form the cyclopentadienyl substituted compounds, including those compounds of the present invention.

Also, according to the present invention, there is provided a catalyst for olefin polymerization comprising:

A. i) a metal complex of formula (II), and ii) an activating cocatalyst, the molar ratio of i) to ii) being from 1:10,000 to 100:1, or B. the reaction product formed by converting a metal complex of formula (II) to an active catalyst by use of an activating technique.

Further according to the present invention there is provided a process for the polymerization of olefins comprising contacting one or more $C_{2-20}$ olefins, including cyclic olefins, under polymerization conditions with a catalyst comprising:

A. i) a metal complex of formula (II), and ii) an activating cocatalyst, the molar ratio of i) to ii) being from 1:10,000 to 100:1, or B. the reaction product formed by converting a metal complex of formula (II) to an active catalyst by use of an activating technique.

The present catalysts and polymerization processes are especially efficient for production of olefin homopolymers, copolymers of two or more olefins, in particular, copolymers of ethylene and a vinylaromatic monomer, such as styrene, and interpolymers of three or more polymerizable monomers over a wide range of polymerization conditions, and especially at elevated temperatures. They are especially useful for the formation of ethylene homopolymers, copolymers of ethylene and one or more higher α-olefins (that is, olefins having 3 or more carbon atoms), copolymers of ethylene, propylene and a diene (EPDM copolymers), copolymers of ethylene and vinylaromatic monomers such as styrene (ES polymers), copolymers of ethylene, styrene, and a diene (ESDM polymers), and copolymers of ethylene, propylene and styrene (EPS polymers). Examples of suitable diene monomers include ethylidenenorbornene, 1,4-hexadiene or similar conjugated or nonconjugated dienes. Surprisingly, the metal complexes of formula (II) demonstrate equivalent or improved catalytic properties compared to metal complexes containing polycyclic, fully aromatic, hydrocarbon ligands, and they and their degradation products are more biologically inert compared to compounds containing fused, polycyclic, fully aromatic hydrocarbon ligands.

The catalysts of this invention may also be supported on a solid material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

The compounds of formula (I) are useful in the formation of the metal complexes of formula (II) as well as in the preparation of other metal complexes. In addition to their use as polymerization catalysts, complexes according to the present invention may be used for hydroformulation, hydrogenation or oligomerization processes.

DETAILED DESCRIPTION OF THE INVENTION

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups. The contents of any patent, patent application or publication referenced herein is hereby incorporated by reference in its entirety herein, especially with respect to its disclosure of organometallic structures, synthetic techniques and general knowledge in the art. As used herein the term "aromatic" refers to a polyatomic, cyclic, ring system containing (4δ+2) π-electrons, wherein δ is an integer greater than or equal to 1. The term "fused" as used herein with respect to two polyatomic, cyclic rings means that such rings have two adjacent atoms thereof common to both rings. The term "fused" as used herein with respect to a ring system containing more than two polyatomic, cyclic rings, means that at least two rings thereof are fused together.

Desirably, in the compounds of the invention, the ring (2) is a 7-membered ring. Even more desirably, the cyclopentadienyl ring (1) and the aromatic ring (3) are not fused together.

Preferred compounds of formula (I) of the invention are those corresponding to the formula:

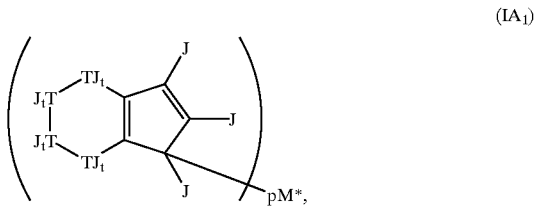

(IA$_1$)

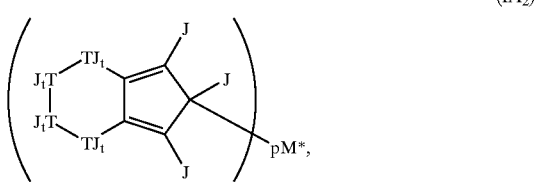

(IA$_2$)

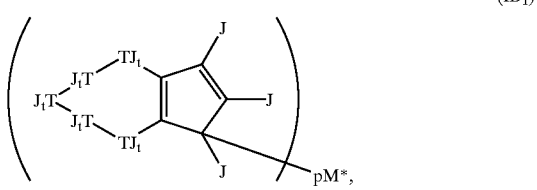

(IB$_1$)

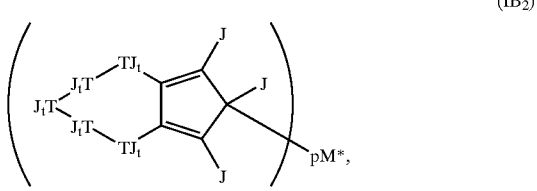

(IB$_2$)

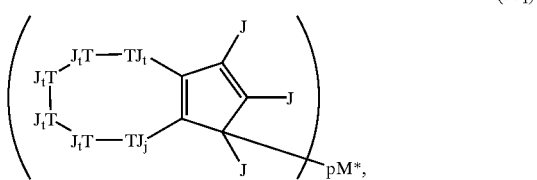

(IC$_1$)

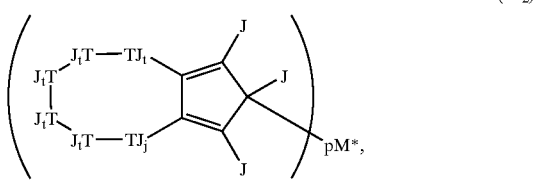

(IC$_2$)

structural isomers thereof wherein one or more double bonds occupy different positions within the various rings, and mixtures thereof, wherein:

T independently each occurrence is carbon, silicon, nitrogen, phosphorus, oxygen, sulfur, or boron;

J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and two J groups together may form a divalent derivative thereby forming a saturated or unsaturated ring, with the proviso that, in at least one occurrence, two or more of the foregoing J groups on different atoms, at least one of which is T, together form a divalent derivative, thereby forming at least one aromatic ring that is fused to the 6, 7, or 8 membered ring;

t is 0, 1 or 2; and, for compounds of formula (1A$_1$) or (1A$_2$) where T is carbon, in at least one occurrence, t is 2; and M* and p are as previously defined.

In the foregoing metal complexes of formula (I), although M* is depicted as being bonded to only one carbon atom of Cp, it is to be understood that when M* is not hydrogen, more than one such carbon atom of Cp may share such bond to M*. The metal complexes of formula (II) include complexes containing 1, 2, or 3 Cp groups, including those wherein two such Cp or other Z groups are bound together by a bridging group. Such complexes are analogous structurally to metallocenes containing 1, 2 or 3 cyclopentadienly groups, or inertly substituted derivatives thereof. Both symmetrical or unsymmetrical compounds are included, that is, compounds containing two dissimilar π-bonded groups, including those containing two Cp groups or a Cp and a π-bonded Z group that is not a Cp group.

Preferred compounds (metal complexes) of formula (II) of the invention are those corresponding to the formula:

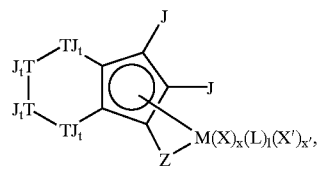

(IIA$_1$)

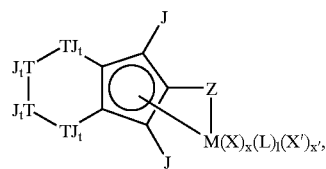

(IIA$_2$)

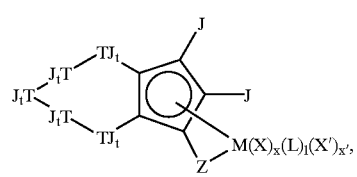

(IIB$_1$)

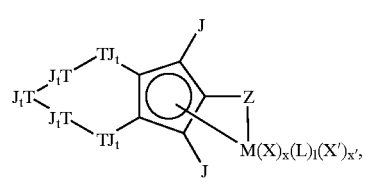

(IIB$_2$)

-continued

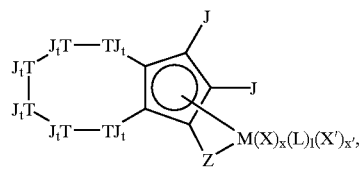

(IIC$_1$)

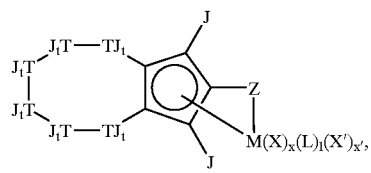

(IIC$_2$)

wherein T, t, J, Z, M, X, L, X', x, I, and X' are as previously defined.

Such complexes include, in particular, complexes containing only one Cp group of the formulas:

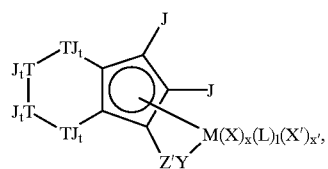

(IIA$^1$$_1$)

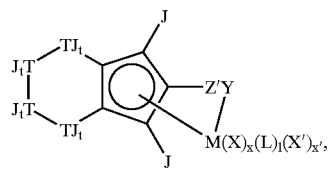

(IIA$^1$$_2$)

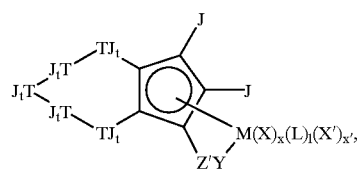

(IIB$^1$$_1$)

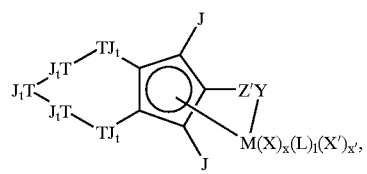

(IIB$^1$$_2$)

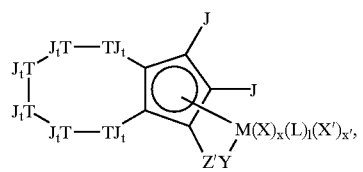

(IIC$^1$$_1$)

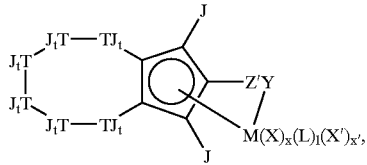
(IIC¹₂)

as well a complexes containing 2 Cp groups of the formulas:

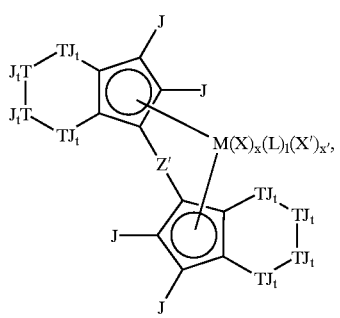
(IIA²₃)

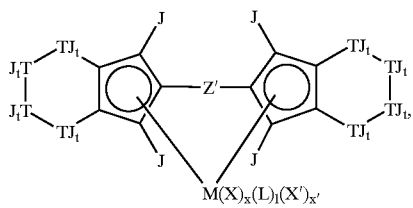
(IIA²₄)

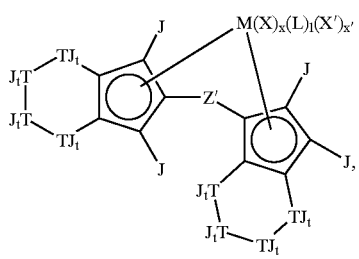
(IIA²₅)

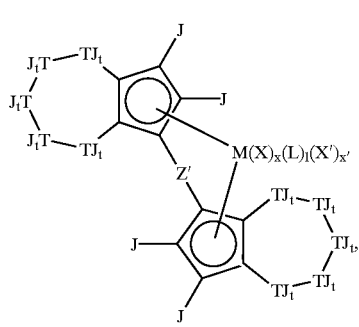
(IIB²₃)

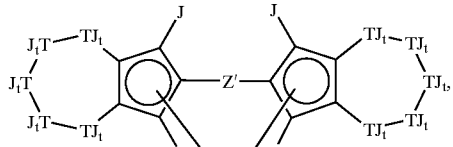
(IIB²₄)

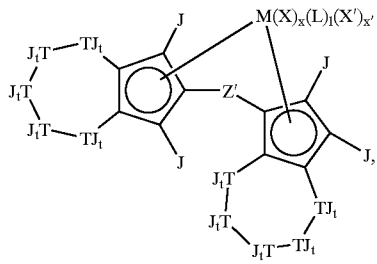
(IIB²₅)

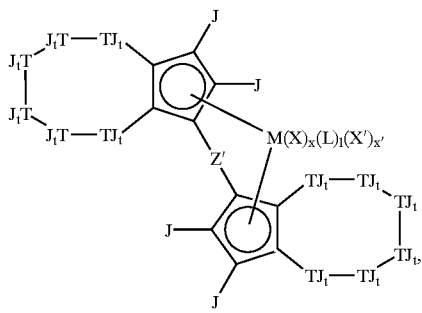
(IIC²₃)

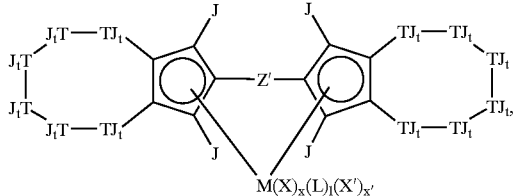
(IIC²₄)

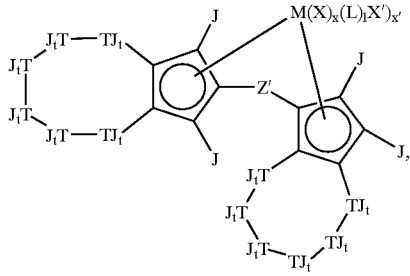
(IIC²₅)

structural isomers thereof wherein one or more double bonds occupy different positions within the various rings, and mixtures thereof, wherein T, J, t, M, Z', X, L, X', x, and X' are as previously defined.

In the metal complexes, preferred L and L" groups are carbon monoxide; phosphines, especially trimethylphosphine, triethylphosphine, triphenylphosphine and bis(1,2-dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including neutral diene L groups are those wherein the metal is in the +2 formal oxidation state.

Further in reference to the metal complexes, X preferably is selected from the group consisting of hydro, halo, hydrocarbyl, silyl, and N,N-dialkylamino-substituted hydrocarbyl. The number of X groups depends on the oxidation state of M, whether Z is divalent or not and whether any neutral diene groups or divalent X' groups are present. The skilled artisan will appreciate that the quantity of the various substituents and the identity of Z are chosen to provide charge balance, thereby resulting in a neutral metal complex. For example, when Z is divalent, and x is zero, X' is two less than the formal oxidation state of M. When Z contains one neutral two electron coordinate-covalent bonding site, and M is in a formal oxidation state of +3, x may equal zero and X' equal 1, or x may equal 2 and X' equal zero. In a final example, if M is in a formal oxidation state of +2, Z may be a divalent ligand group, whereupon x and x' are both equal to zero and one neutral L ligand group may be present.

Highly preferred compounds of formula (I) correspond to the formula:

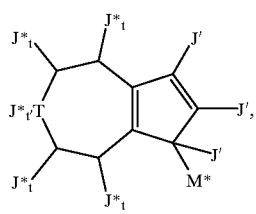
(IB$^a{}_1$)

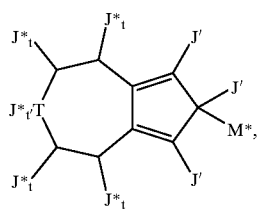
(IB$^a{}_2$)

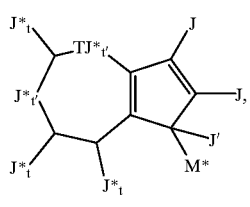
(IB$^b{}_1$)

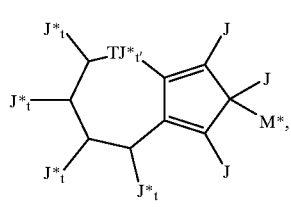
(IB$^b{}_2$)

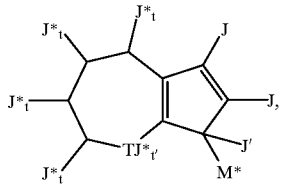
(IB$^{b'}{}_1$)

structural isomers thereof wherein one or more double bonds occupy different positions within the various rings, and mixtures thereof, wherein J* independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J* group having up to 40 atoms not counting hydrogen atoms, and two J* groups together or a J* and a J' group together may form a divalent derivative thereby forming a saturated or unsaturated ring, with the proviso that, in at least one occurrence, two or more of the foregoing J* groups on different atoms, together form a divalent derivative, thereby forming at least one aromatic ring that is fused to the 6, 7, or 8 membered ring;

J' independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J' group having up to 40 atoms not counting hydrogen atoms, and two J' groups together or a J' group and a J* group together may form a divalent derivative thereby forming a saturated or unsaturated fused ring;

M* is hydrogen, an alkali metal or an alkaline earth metal halide,

T is carbon, boron, nitrogen or oxygen, t is 1 or 2; and t' is 0, 1 or 2.

The corresponding preferred compounds of formula (II) are of the formula:

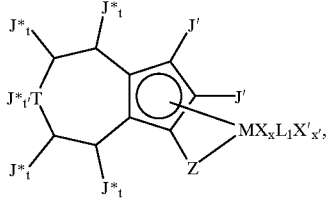
(IIBa₁)

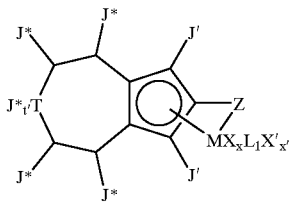
(IIBa₂)

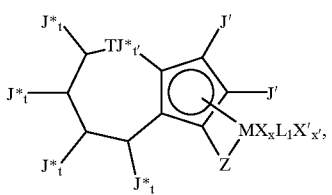
(IIBb₁)

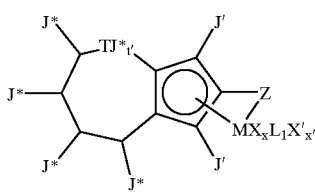
(IIBb₂)

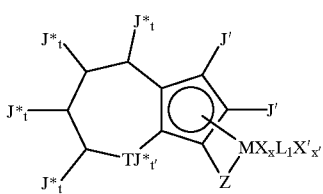
(IIBb′₁)

structural isomers thereof wherein one or more double bonds occupy different positions within the various rings, and mixtures thereof, wherein Z, M, X, L, X', x, ., x', T, J*, J', t, and t' are as previously defined More highly preferred compounds and metal complexes according to the present invention correspond to the formulas:

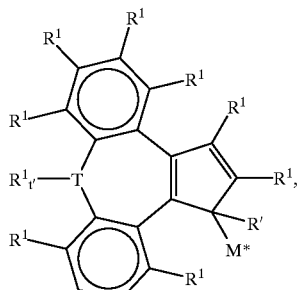

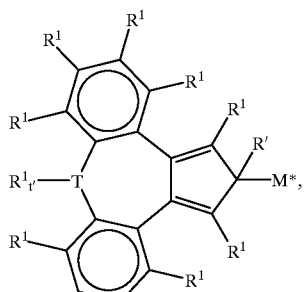

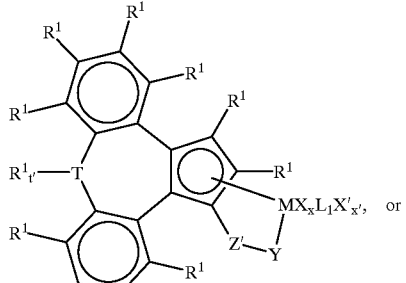
or

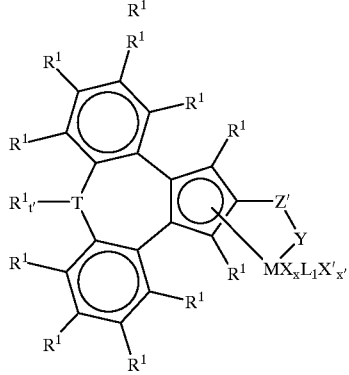

wherein
T is carbon, or nitrogen;
when T is carbon, t' is 2, and when T is nitrogen, t' is 1;
M* is hydrogen, sodium, potassium or lithium;
M is titanium;
$R^1$ each occurrence is hydrogen or a hydrocarbyl, hydrocarbyloxy, dihydrocarbylamino, hydrocarbyleneamino, dihydrocarbylamino-substituted hydrocarbyl group, or hydrocarbyleneamino-substituted hydrocarbyl group of up to 20 atoms not counting hydrogen, and optionally two $R^1$ groups may be joined together;

Y is —O—, —S—, —NR$^5$-, —PR$^5$-; —NR$^5{}_2$, or —PR$^5{}_2$;

Z' is SiR$^6{}_2$, CR$^6{}_2$, SiR$^6{}_2$SiR$^6{}_2$, CR$^6{}_2$CR$^6{}_2$, CR$^6$=CR$^6$, CR$^6{}_2$SiR$^6{}_2$, BR$^6$, BR$^6$L", or GeR$^6{}_2$;

R$^5$ each occurrence is independently hydrocarbyl, trihydrocarbylsilyl, or trihydrocarbylsilylhydrocarbyl, said R$^5$ having up to 20 atoms other than hydrogen, and optionally two R$^5$ groups or R$^5$ together with Y form a ring system;

R$^6$ each occurrence is independently hydrogen, or a member selected from hydrocarbyl, hydrocarbyloxy, silyl, halogenated alkyl, halogenated aryl, —NR$^5{}_2$, and combinations thereof, said R$^6$ having up to 20 non-hydrogen atoms, and optionally, two R$^6$ groups form a ring system;

X, L, and X' are as previously defined;

x is 0, 1 or 2;

l is 0 or 1; and

X' is 0 or 1;

with the proviso that:

when x is 2, X' is zero, M is in the +4 formal oxidation state (or M is in the +3 formal oxidation state if Y is —NR$^5{}_2$ or —PR$^5{}_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and X' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and X' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when x and X' are both 0, I is 1, M is in the +2 formal oxidation state, and L is a neutral, conjugated or nonconjugated diene, optionally substituted with one or more hydrocarbyl groups, said L having up to 40 carbon atoms and being bound to M by means of delocalized π-electrons thereof.

Most highly preferably, R$^1$ each occurrence is hydrogen,

Z is NR$^5$ wherein R$^5$ is C$_{1-10}$ alkyl or cycloalkyl; and

Z' is dimethylsilane; with the proviso that:

when x is 2, 1 and X' are both zero, M is in the +4 formal oxidation state, and X is independently each occurrence methyl, benzyl, or halide;

when x and 1 are zero, X' is one, and M is in the +4 formal oxidation state, X' is a 1,4-butadienyl group that forms a metallocyclopentene ring with M, when x is 1, I and X' are zero, M is in the +3 formal oxidation state, and X is 2-(N,N-dimethylamino)benzyl; and when x and X' are 0, 1 is 1, M is in the +2 formal oxidation state, and L is 1,4-diphenyl-1,3-butadiene or 1,3-pentadiene.

Specific examples of metal complexes of formula (I) are:

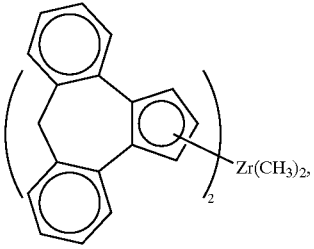

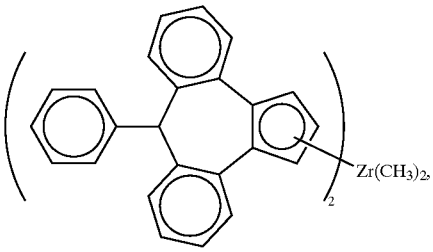

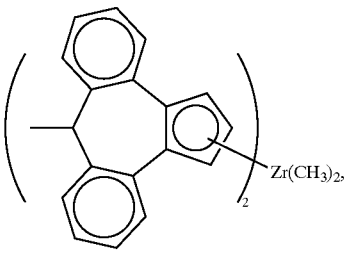

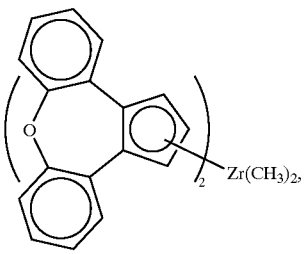

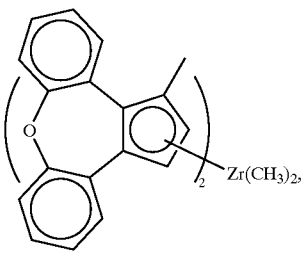

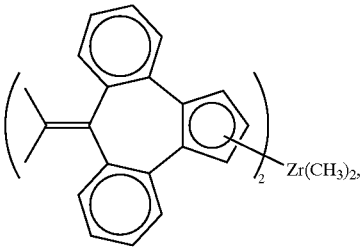

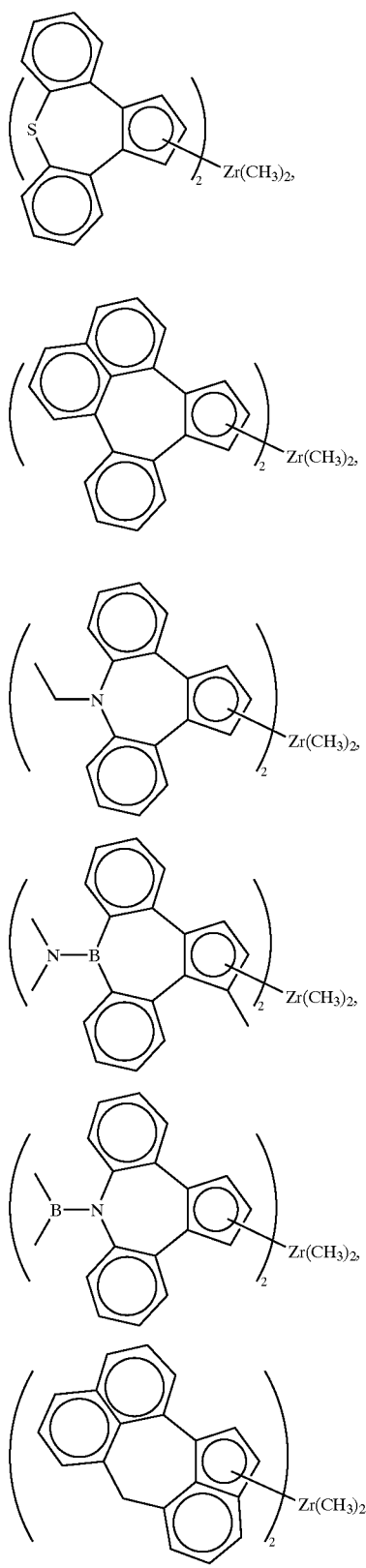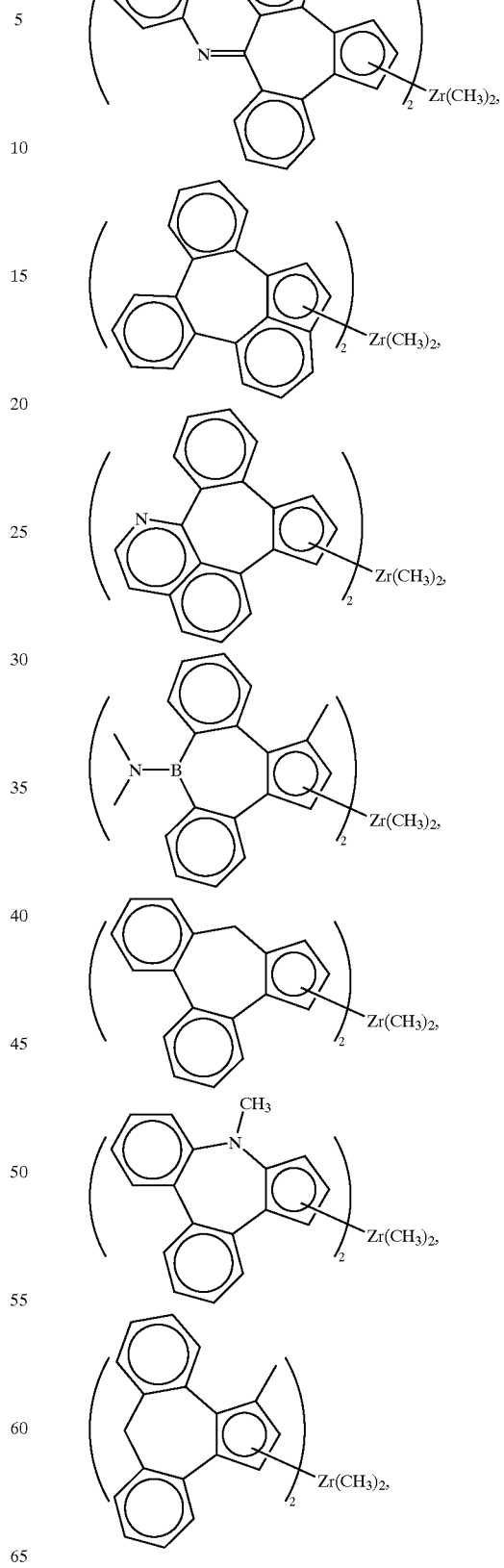

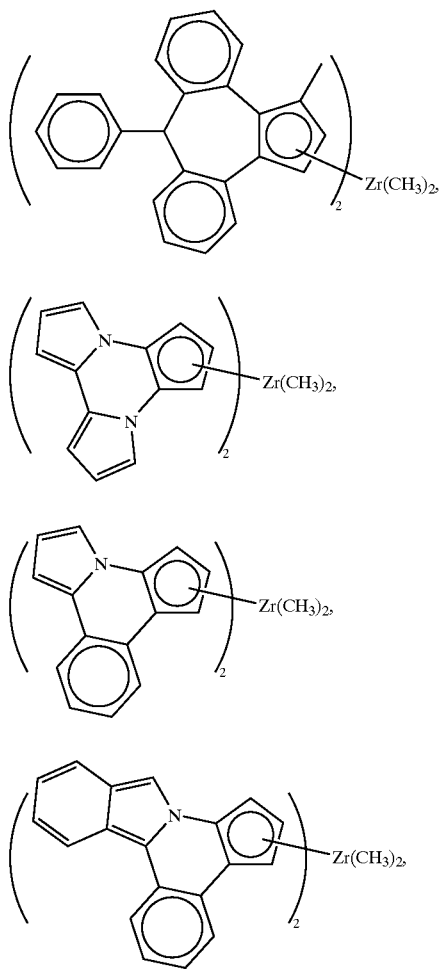
Specific examples of metal complexes of formula (II) are:
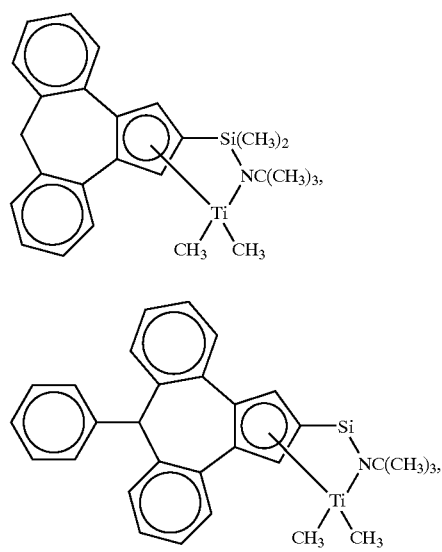
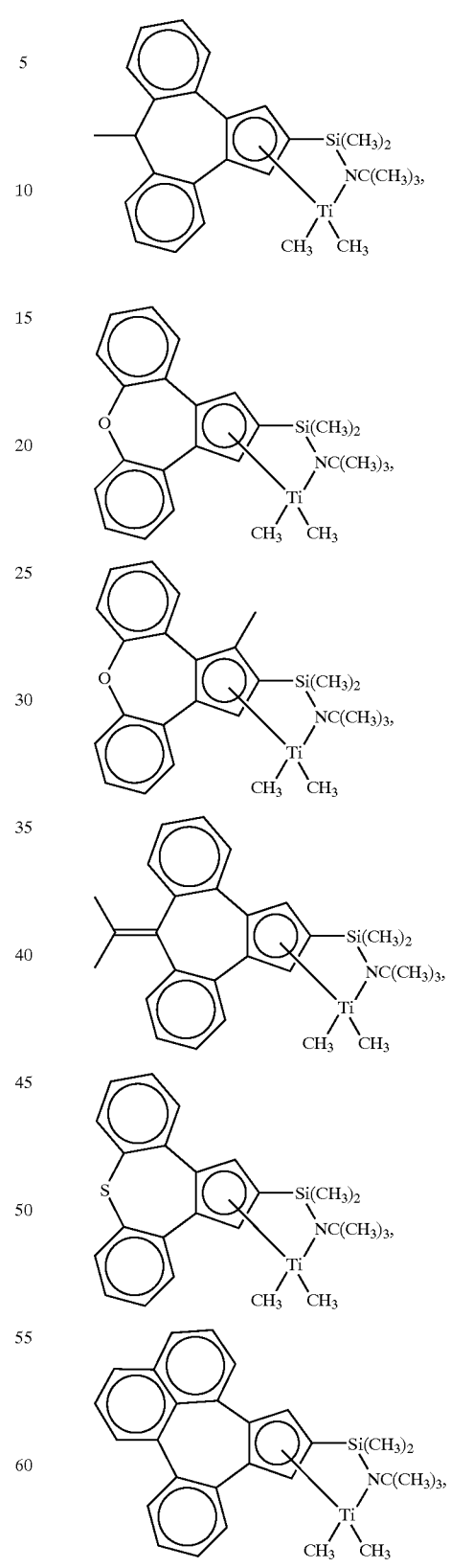

-continued
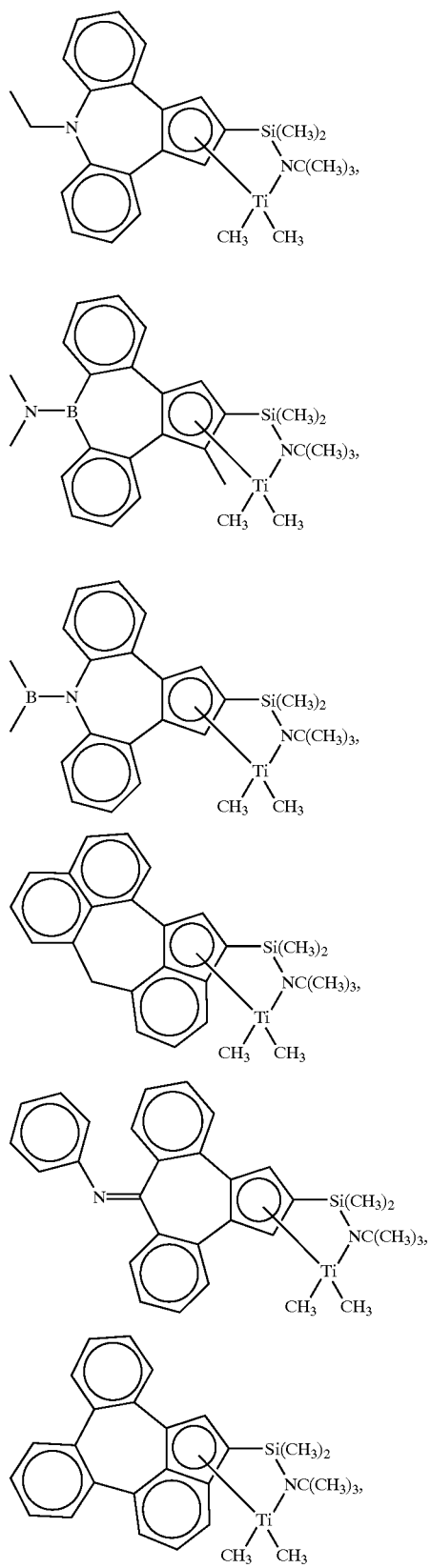
-continued
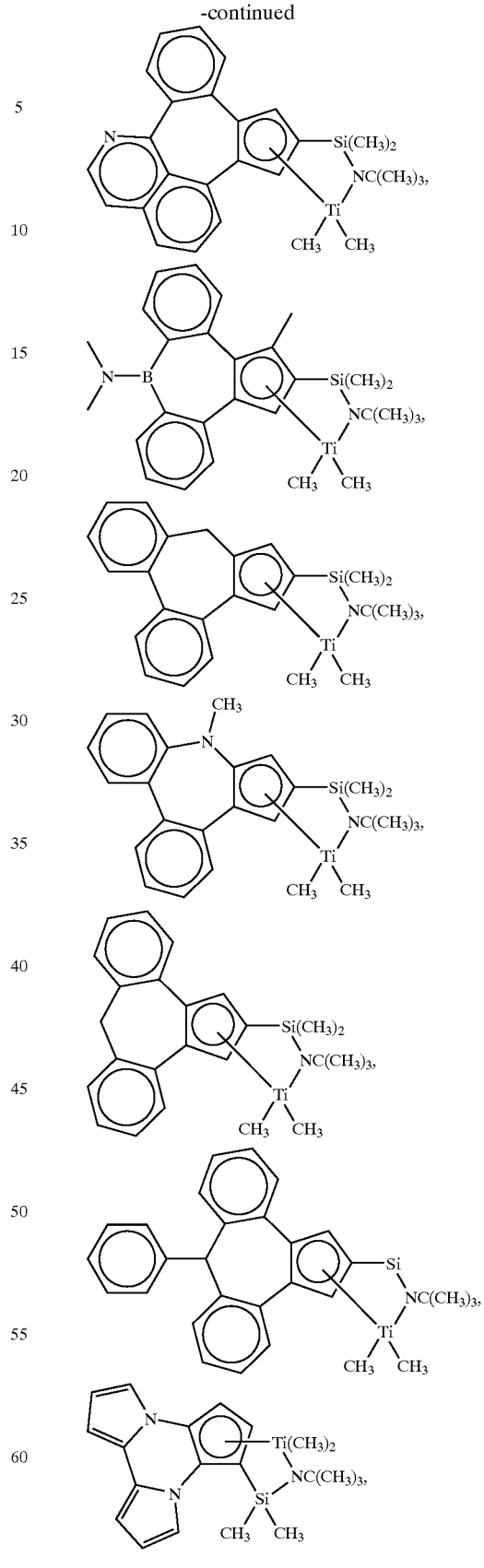

21
-continued

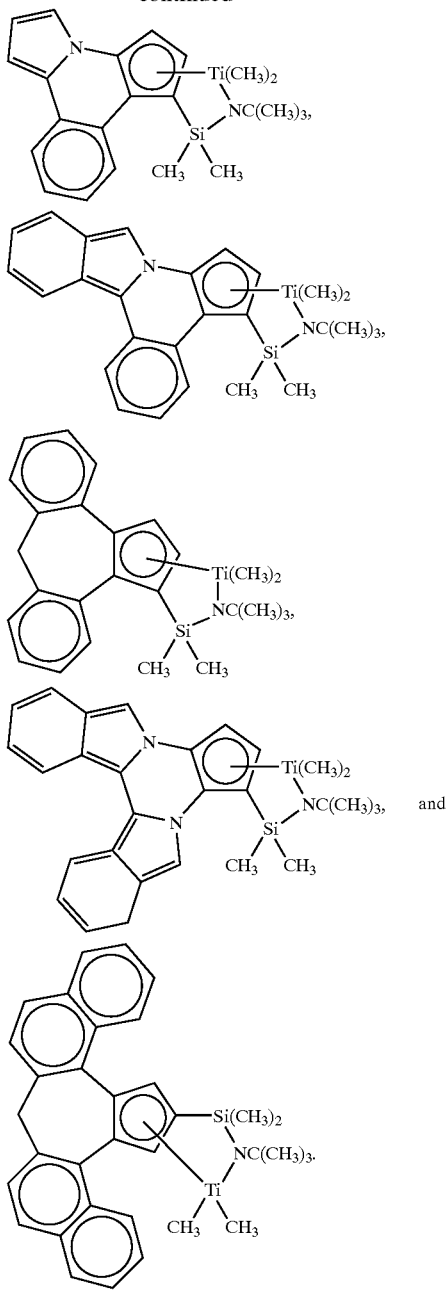

The present process for forming a polycyclic, fused ring cyclopentadiene compound (III), in a preferred embodiment involves the following steps:

A) contacting
1) a cyclic compound containing ethylenic unsaturation in the ring forming atoms thereof and substituted at the α-position of such ethylenic unsaturation with a leaving group with
2) an acetylenic compound containing a protecting group at one of the acetylenic carbons and a group that is reactive with the leaving group of the cyclic compound at the remaining acetylenic carbon under conditions to cause ligand exchange, optionally in the presence of a base, thereby forming a cyclic compound containing ethylenic unsaturation and substituted at an α-carbon of the ethylenic unsaturation with an acetylenic group;

22

B) carbonylating and ring closing the product of step A) to form a polycyclic, fused ring cyclopentenone compound; and C) reducing and dehydrating the product of step B) to form the desired polycyclic, fused ring cyclopentadiene compound (III).

While the present process is applicable to the preparation of a wide variety of polycyclic, fused ring cyclopentadiene compounds, preferred products are those previously disclosed as being novel.

The process is further illustrated schematically as follows:

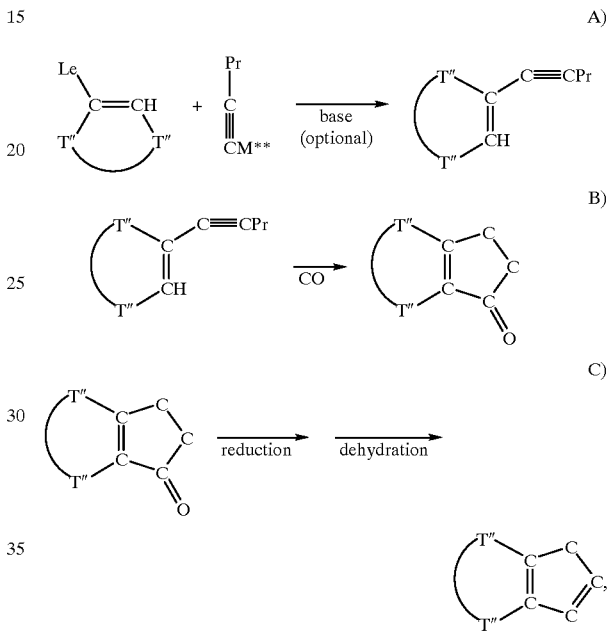

where Le is a leaving group, preferably halogen, most preferably Br,

Pr is a protecting group, preferably tri($C_{1-10}$ hydrocarbyl) silyl, more preferably $SiR^2_3$, where $R^2$ is $C_{1-10}$ alkyl or cycloalkyl, and most preferably $R^2$ is $C_{1-4}$ alkyl, T"—T" is the divalent remnant of the cyclic compound containing ethylenic unsaturation excluding the carbons forming the ethylenic unsaturation and Le, and M** is a group that is reactive with the leaving group, Le, preferably an alkali metal, an alkaline earth metal halide or an alkaline earth metal hydrocarbyl.

Desirably, the present process may be employed to prepare polycyclic, fused ring cyclopentadiene compounds (III) in which one of the rings fused to the cyclopentadiene group is not an aromatic ring, preferably one that contains 7 or more ring atoms, preferably carbons. More desirably still, the compounds prepared by the present process comprise both the foregoing, non-aromatic ring containing 7 or more ring atoms and at least one aromatic ring fused thereto. Even more desirably the cyclopentadiene ring and the aromatic rings are not fused together.

Preferred cyclic compounds containing ethylenic unsaturation used in step 1) of the present process correspond to the formula:

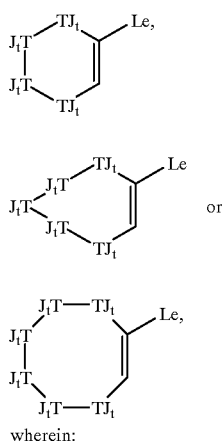

wherein:

T independently each occurrence is carbon, silicon, nitrogen, phosphorus, oxygen, sulfur, or boron;

J independently each occurrence is hydrogen, hydrocarbyl, trihydrocarbylsilyl, trihydrocarbylgermyl, halide, hydrocarbyloxy, trihydrocarbylsiloxy, bis (trihydrocarbylsilyl)amino, di(hydrocarbyl)amino, hydrocarbyleneamino, hydrocarbylimino, di(hydrocarbyl) phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis (trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and optionally two J groups together may form a divalent derivative thereby forming a saturated or unsaturated ring;

In a preferred embodiment, in the foregoing formulas t is 0, 1 or 2; and, for compounds of formula $1A_1$) or $1A_2$) where T each occurrence is carbon, in at least one occurrence, t is 2. In an even more preferred embodiment, in at least one occurrence, two or more of the foregoing J groups on different atoms, at least one of which is T, together form a divalent derivative, thereby forming at least one aromatic ring that is fused to the 6, 7, or 8 membered ring.

The initial cyclic, ethylenically unsaturated reagents 1) are known compounds or may be prepared according to well known techniques from known compounds. The cyclopentenone formation, step A), is similar to the process disclosed in *J. Org. Chem.*, 1988, 53, 2493, and is preferably conducted at temperatures from 0 to 100° C., pressures from 50 kPa to 5000 kPa, in an inert diluent. The optional base is preferably a Lewis base compound, especially an organic amine, an organic phosphine, or a mixture thereof. A catalyst, especially a palladium or platinum halide or a mixture thereof in combination with a reduced copper salt, that is a Cu(II) salt, may also be employed as well. Reaction times from a few minutes to several hours are normally used. A highly desirably acetylenic reagent 2) is (trimethylsilyl) acetylene.

The carbonylation and ring closure, step B), is desirably conducted at elevated pressures and temperatures in the presence of carbon monoxide and a metal catalyst, especially a platinum or rhodium salt. Suitable temperatures are from 50° C. to 250° C. Suitable pressures are from 500 kPa to 20 MPa, preferably from 1 MPa to 10 MPa. The reaction is desirably conducted in an aqueous diluent also comprising one or more Lewis base compounds, especially organic amines, phosphines, or mixtures thereof. Reaction times of one to 20 hours are normally used.

The reduction and dehydration processes comprising step C) are preferably conducted sequentially and may or may not involve recovery and purification of the intermediate, reduced product prior to dehydration. Suitable conditions of temperature and pressure are from 0° C. to 100° C. and from 50 kPa to 5000 kPa. A suitable reaction medium is a mixture of a chlorinated hydrocarbon and an alcohol. A preferred reducing agent is sodium borohydride. Reaction times from 15 minutes to 20 hours may be employed. Dehydration is accomplished by use of mild dehydrating conditions, such as contacting with dilute aqueous HCl at temperatures from 0° C. to 100° C. and pressures from 50 kPa to 5000 kPa. The product is generally soluble in hydrocarbons or chlorohydrocarbons and is readily recovered by extraction with such a solvent followed by removal of solvent.

Specific examples of compounds of formula (III) prepared according to the invention are:

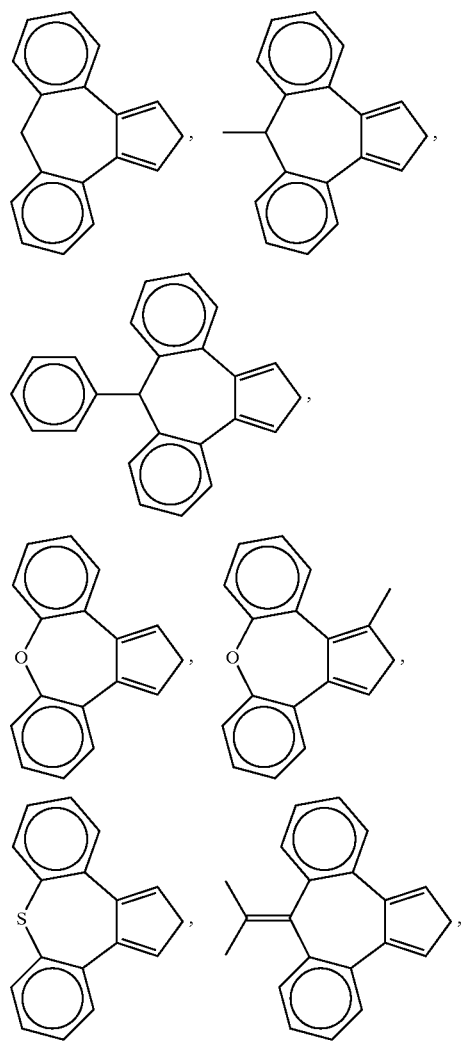

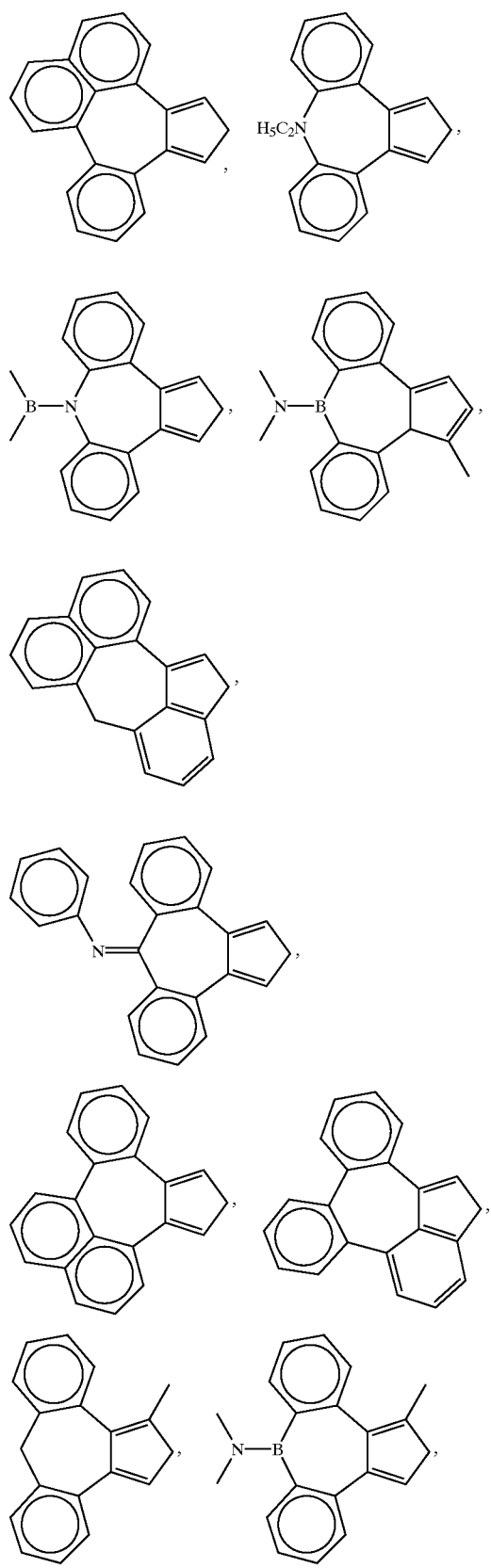
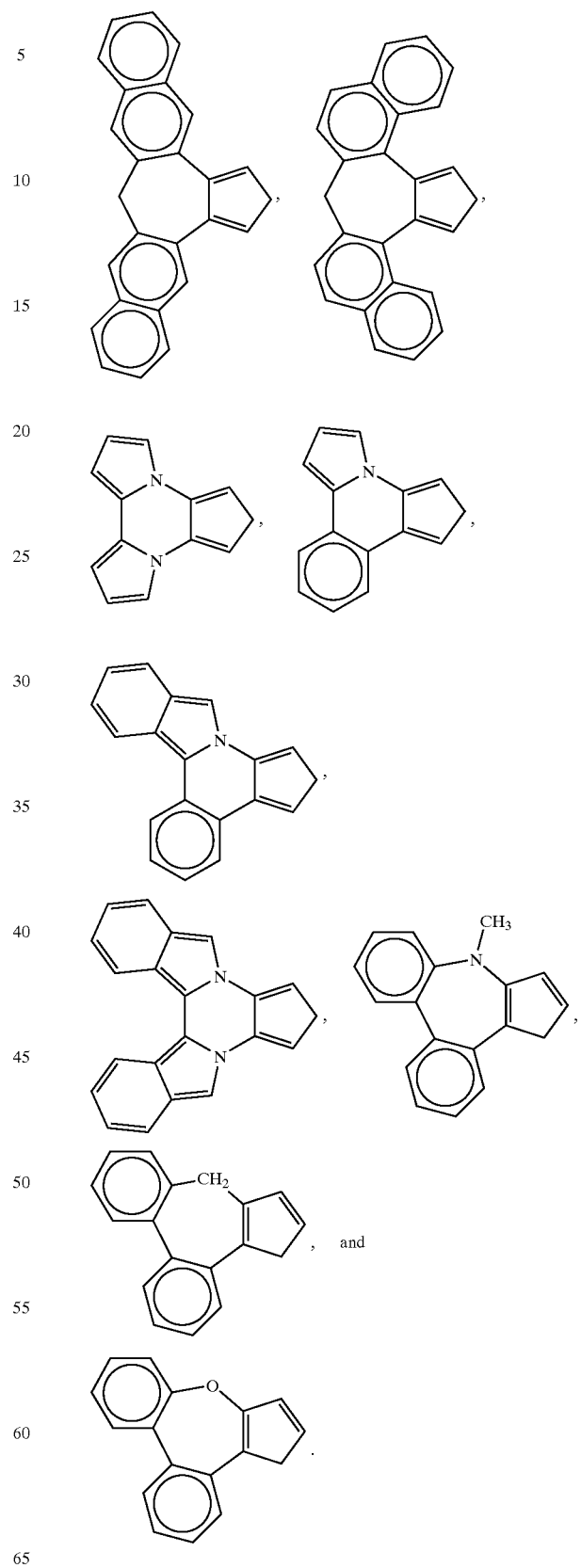

Formation of metal complexes from the neutral polycyclic, fused ring cyclopentadiene compounds (III) is straightforward, using standard techniques of ligand formation and organometallic synthesis. Preferably it is readily accomplished by contacting the neutral compound with an alkalimetal hydrocarbyl compound, an alkaline earth metal dihydrocarbyl compound, or an alkaline earth metal hydrocarbyl halide compound, followed by reaction with a transition metal halide or amide in an inert diluent. Ligand groups, such as silaneamido functionality may be added to the polycyclic, fused ring cyclopentadiene compounds prior to addition of the transition metal where required. Optionally a reducing agent can be employed to produce the lower oxidation state complexes, and standard ligand exchange procedures can by used to produce different ligand substituents. Processes that are suitably adapted for use herein are well known to synthetic organometallic chemists.

The foregoing syntheses are preferably conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

Illustrative polycyclic cyclopentadiene compounds that may be prepared according to the present invention include: azulene, hexahydroazulene, 2,4-dimethylazulene, 2,4-dimethylhexahydroazulene, 2,8-dihydrodibenzo[e,h]azulene, and mixtures thereof, especially mixtures of positional isomers.

Illustrative metal complexes that may be employed in the practice of the present invention include:

(2,8-dihydrodibenzo[e,h]azulen-2-yl)-N-(1,1-dimethylethyl)dimethyl-silanamide titanium (II) 1,4-diphenyl-1,3-butadiene, (2,8-dihydrodibenzo[e,h]azulen-2-yl)-N-(1,1-dimethylethyl)dimethyl-silanamide titanium (II) 1,3-pentadiene, ((2,8-dihydrodibenzo[e,h]azulen-2-yl)-N-(1,1-dimethylethyl)dimethyl-silanamide titanium (III) 2-(N,N-dimethylamino)benzyl, (2,8-dihydrodibenzo[e,h]azulen-2-yl)-N-(1,1-dimethylethyl)dimethyl-silanamide titanium (IV) dichloride, 2,8-dihydrodibenzo[e,h]azulen-2-yl)-N-(1,1-dimethylethyl)dimethyl-silanamide titanium (IV) dimethyl, 2,8-dihydrodibenzo[e,h]azulen-2-yl)-N-(1,1-dimethylethyl)dimethyl-silanamide titanium (IV) dibenzyl, (2,8-dihydrodibenzo[e,h]azulen-2-yl)-N-(cyclohexyl)dimethyl-silanamide titanium (II) 1,4-diphenyl-1,3-butadiene, (2,8-dihydrodibenzo[e,h]azulen-2-yl)-N-(cyclohexyl)dimethyl-silanamide titanium (II) 1,3-pentadiene, ((2,8-dihydrodibenzo[e,h]azulen-2-yl)-N-(cyclohexyl)dimethyl-silanamide titanium (III) 2-(N,N-dimethylamino)benzyl, (2,8-dihydrodibenzo[e,h]azulen-2-yl)-N-(cyclohexyl)dimethyl-silanamide titanium (IV) dichloride, 2,8-dihydrodibenzo[e,h]azulen-2-yl)-N-(cyclohexyl)dimethyl-silanamide titanium (IV) dimethyl, 2,8-dihydrodibenzo[e,h]azulen-2-yl)-N-(cyclohexyl)dimethyl-silanamide titanium (IV) dibenzyl, (2,8-dihydrodibenzo[e,h]azulen-1-yl)-N-(1,1-dimethylethyl)dimethyl-silanamide titanium (II) 1,4-diphenyl-1,3-butadiene, (2,8-dihydrodibenzo[e,h]azulen-1-yl)-N-(1,1-dimethylethyl)dimethyl-silanamide titanium (II) 1,3-pentadiene, ((2,8-dihydrodibenzo[e,h]azulen-1-yl)-N-(1,1-dimethylethyl)dimethyl-silanamide titanium (III) 2-(N,N-dimethylamino)benzyl, (2,8-dihydrodibenzo[e,h]azulen-1-yl)-N-(1,1-dimethylethyl)dimethyl-silanamide titanium (IV) dichloride, 2,8-dihydrodibenzo[e,h]azulen-1-yl)-N-(1,1-dimethylethyl)dimethyl-silanamide titanium (IV) dimethyl, 2,8-dihydrodibenzo[e,h]azulen-1-yl)-N-(1,1-dimethylethyl)dimethyl-silanamide titanium (IV) dibenzyl, (2,8-dihydrodibenzo[e,h]azulen-1-yl)-N-(cyclohexyl)dimethyl-silanamide titanium (II) 1,4-diphenyl-1,3-butadiene, (2,8-dihydrodibenzo[e,h]azulen-1-yl)-N-(cyclohexyl)dimethyl-silanamide titanium (II) 1,3-pentadiene, ((2,8-dihydrodibenzo[e,h]azulen-1-yl)-N-(cyclohexyl)dimethyl-silanamide titanium (III) 2-(N,N-dimethylamino)benzyl, (2,8-dihydrodibenzo[e,h]azulen-1-yl)-N-(cyclohexyl)dimethyl-silanamide titanium (IV) dichloride, 2,8-dihydrodibenzo[e,h]azulen-1-yl)-N-(cyclohexyl)dimethyl-silanamide titanium (IV) dimethyl, 2,8-dihydrodibenzo[e,h]azulen-1-yl)-N-(cyclohexyl)dimethyl-silanamide titanium (IV) dibenzyl, and mixtures thereof, especially mixtures of positional isomers.

The skilled artisan will recognize that additional members of the foregoing list, obtainable by substitution of known ligands or different Group 3–10 metals for those specifically named, are also included within the invention. Moreover, it should also be recognized that all possible electronic distributions within the molecule, such as $\eta^3$, $\eta^4$ or $\eta^5$ are intended to be included by the foregoing named compounds.

The complexes can be prepared by combining a metal halide salt with the corresponding fused, polycyclic ring system ligand dianion in an inert diluent, or by combining a metal amide with the corresponding neutral fused, polycyclic ring system in an inert diluent. Optionally a reducing agent can be employed to produce the lower oxidation state complexes, and standard ligand exchange procedures can by used to produce different ligand substituents. Processes that are suitably adapted for use herein are well known to synthetic organometallic chemists. The syntheses are preferably conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof, aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri (hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. A preferred ion forming compound is a tri($C_{1-20}$-hydrocarbyl)ammonium salt of a tetrakis (fluoroaryl)borate, especially a tetrakis(pentafluorophenyl) borate. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and U.S. Ser. No.09/251,664, filed Feb. 17, 1999 (WO99/42467).

Combinations of neutral Lewis acids, especially the combination of a trialkylaluminum compound having from 1 to 4 carbons in each alkyl group and a halogenated tri (hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^−$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

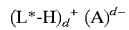

wherein:
L* is a neutral Lewis base;
(L*-H)$^+$ is a conjugate Bronsted acid of L*;
$A^{d−}$ is a noncoordinating, compatible anion having a charge of d-, and
d is an integer from 1 to 3.

More preferably $A^{d−}$ corresponds to the formula: $[M'Q_4]^−$; wherein:
M' is boron or aluminum in the +3 formal oxidation state; and
Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is A-. Activating cocatalysts comprising boron which are particularly useful in the preparation of catalysts of this invention may be represented by the following general formula:

$$(L^*-H)^+(BQ_4)^-;$$

wherein:

L* is as previously defined;

B is boron in a formal oxidation state of 3; and

Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkyl-ammonium- or dialkylarylammonium-salts containing one or more $C_{12-40}$ alkyl groups. The latter cocatalysts have been found to be particularly suitable for use in combination with not only the present metal complexes but other Group 4 metallocenes as well.

Illustrative, but not limiting, examples of boron compounds which may be used as an activating cocatalyst in the preparation of the improved catalysts of this invention (as well as previously known Group 4 metal catalysts) are tri-substituted ammonium salts such as:

trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(sec-butyl)ammonium tetrakis(pentafluorophenyl) borate, N,N-dimethylanilinium tetrakis(pentafluorophenyl) borate, N,N-dimethylanilinium n-butyltris(pentafluorophenyl) borate, N,N-dimethylanilinium benzyltris(pentafluorophenyl) borate, N,N-dimethylanilinium tetrakis(4-(t-butyldimethylsilyl)-2, 3, 5, 6-tetrafluorophenyl) borate, N,N-dimethylanilinium tetrakis(4-(triisopropylsilyl)-2, 3, 5, 6-tetrafluorophenyl) borate, N,N-dimethylanilinium pentafluorophenoxytris (pentafluorophenyl) borate, N,N-diethylanilinium tetrakis(pentafluorophenyl) borate, N,N-dimethyl-2,4,6-trimethylanilinium tetrakis (pentafluorophenyl) borate, dimethyltetradecylammonium tetrakis (pentafluorophenyl) borate, dimethylhexadecylammonium tetrakis (pentafluorophenyl) borate, dimethyloctadecylammonium tetrakis (pentafluorophenyl) borate, methylditetradecylammonium tetrakis (pentafluorophenyl) borate, methylditetradecylammonium (hydroxyphenyl)tris (pentafluorophenyl) borate, methylditetradecylammonium (diethylaluminoxyphenyl) tris(pentafluorophenyl) borate, methyldihexadecylammonium tetrakis (pentafluorophenyl) borate, methyldihexadecylammonium (hydroxyphenyl)tris (pentafluorophenyl) borate, methyldihexadecylammonium (diethylaluminoxyphenyl) tris(pentafluorophenyl) borate, methyldioctadecylammonium tetrakis (pentafluorophenyl) borate, methyldioctadecylammonium (hydroxyphenyl)tris (pentafluorophenyl) borate, methyldioctadecylammonium (diethylaluminoxyphenyl) tris(pentafluorophenyl) borate, methyldioctadecylammonium tetrakis (pentafluorophenyl) borate, phenyldioctadecylammonium tetrakis(pentafluorophenyl) borate, phenyldioctadecylammonium (hydroxyphenyl)tris (pentafluorophenyl) borate, phenyldioctadecylammonium (diethylaluminoxyphenyl) tris(pentafluorophenyl) borate, (2,4,6-trimethylphenyl)dioctadecylammonium tetrakis (pentafluorophenyl) borate, (2,4,6-trimethylphenyl)dioctadecylammonium (hydroxyphenyl)tris(pentafluorophenyl)-borate, (2,4,6-timethylphenyl)dioctadecylammonium (diethylaluminoxypheny) tris(pentafluorophenyl)borate, (2,4,6-trifluorophenyl)dioctadecylammonium tetrakis (pentafluorophenyl)borate, (2,4,6-trifluorophenyl)dioctadecylammonium (hydroxyphenyl)tris(pentafluorophenyl)-borate, (2,4,6-trifluorophenyl)dioctadecylammonium (diethylaluminoxyphenyl)tris(pentafluoro-phenyl) borate, (pentafluorophenyl)dioctadecylammonium tetrakis (pentafluorophenyl)borate, (pentafluorophenyl)dioctadecylammonium (hydroxyphenyl)tris(pentafluorophenyl)-borate, (pentafluorophenyl)dioctadecylammonium (diethylaluminoxyphenyl)tris(pentafluoro-phenyl) borate, (p-trifluoromethylphenyl)dioctadecylammonium tetrakis (pentafluorophenyl)borate, (p-trifluoromethylphenyl)dioctadecylammonium (hydroxyphenyl)tris(pentafluoro-phenyl) borate, (p-trifluoromethylphenyl)dioctadecylammonium (diethylaluminoxyphenyl)tris(pentafluorophenyl) borate, p-nitrophenyldioctadecylammonium tetrakis (pentafluorophenyl)borate, p-nitrophenyldioctadecylammonium (hydroxyphenyl)tris (pentafluorophenyl) borate, p-nitrophenyldioctadecylammonium (diethylaluminoxyphenyl)tris(pentafluorophenyl) borate, and mixtures of the foregoing, dialkyl ammonium salts such as:

di-(i-propyl)ammonium tetrakis(pentafluorophenyl) borate, methyloctadecylammonium tetrakis (pentafluorophenyl) borate, methyloctadodecylammonium tetrakis(pentafluorophenyl) borate, and dioctadecylammonium tetrakis(pentafluorophenyl) borate;

tri-substituted phosphonium salts such as:
triphenylphosphonium tetrakis(pentafluorophenyl) borate, methyldioctadecylphosphonium tetrakis(pentafluorophenyl) borate, and tri(2,6-dimethylphenyl)phosphonium tetrakis(pentafluorophenyl) borate;
di-substituted oxonium salts such as:
diphenyloxonium tetrakis(pentafluorophenyl) borate, di(o-tolyl)oxonium tetrakis(pentafluorophenyl) borate, and di(octadecyl)oxonium tetrakis(pentafluorophenyl) borate;
di-substituted sulfonium salts such as:
di(o-tolyl)sulfonium tetrakis(pentafluorophenyl) borate, and methylcotadecylsulfonium tetrakis(pentafluorophenyl) borate.

Preferred trialkylammonium cations are methyldioctadecylammonium and dimethyloctadecylammonium. The use of the above Bronsted acid salts as activating cocatalysts for addition polymerization catalysts is known in the art, having been disclosed in U.S. Pat. Nos. 5,064,802, 5,919,983, 5,783,512 and elsewhere. Preferred dialkylarylammonium cations are fluorophenyldioctadecylammonium-, perfluorophenyldioctacecylammonium- and p-trifluoromethylphenyldi(octadecyl)ammonium cations. It should be noted that certain of the cocatalysts, especially those containing a hydroxyphenyl ligand in the borate anion, may require the addition of a Lewis acid, especially a trialkylaluminum compound, to the polymerization mixture or the catalyst composition, in order to form the active catalyst composition.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:
$Ox^{e+}$ is a cationic oxidizing agent having a charge of $e^+$;
e is an integer from 1 to 3; and
$A^{d-}$ and d are as previously defined.

Examples of cationic oxidizing agents include: ferrocenium, hydrocarbyl-substituted ferrocenium, $Ag^+$ or $Pb^{+2}$. Preferred embodiments of $A^{d-}$ are those anions previously defined with respect to the Bronsted acid containing activating cocatalysts, especially tetrakis(pentafluorophenyl)borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

$$\text{©}^+ A^-$$

wherein:
$\text{©}^+$ is a $C_{1-20}$ carbenium ion; and
A is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

$$R^3{}_3Si(X')_q{}^+ A^-$$

wherein:
$R^3$ is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula: $(A^{1+a^1})_{b^1}(Z^1J^1{}_{j^1})^{-c^1}d^1$, wherein:
$A^1$ is a cation of charge $+a^1$,
$Z^1$ is an anion group of from 1 to 50, preferably 1 to 30 atoms, not counting hydrogen atoms, further containing two or more Lewis base sites;
$J^1$ independently each occurrence is a Lewis acid coordinated to at least one Lewis base site of $Z^1$, and optionally two or more such $J^1$ groups may be joined together in a moiety having multiple Lewis acidic functionality,
$j^1$ is a number from 2 to 12 and
$a^1, b^1, c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

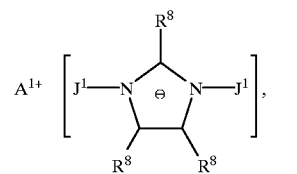

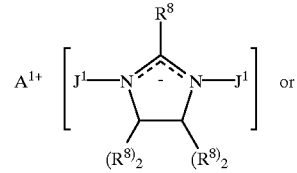 or

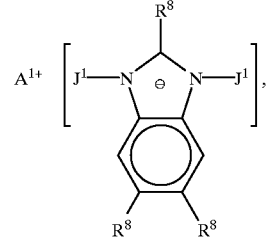

wherein:
$A^{1+}$ is a monovalent cation as previously defined, and preferably is a trihydrocarbyl ammonium cation, containing one or two $C_{10-40}$ alkyl groups, especially the methylbis(tetradecyl)ammonium- or methylbis(octadecyl)ammonium-cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris(pentafluorophenyl)aluminane.

Examples of these catalyst activators include the trihydrocarbylammonium-, especially, methylbis(tetradecyl)ammonium- or methylbis(octadecyl)ammonium-salts of:

bis(tris(pentafluorophenyl)borane)imidazolide,
bis(tris(pentafluorophenyl)borane)-2-undecylimidazolide, bis(tris(pentafluorophenyl)borane)-2-heptadecylimidazolide, bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl)imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-2-heptadecylimidazolinide,
bis(tris(pentafluorophenyl)alumane)-4,5-bis(undecyl)imidazolinide,
bis(tris(pentafluorophenyl)alumane)-2-unhepatdecylimidazolinide,
bis(tris(pentafluorophenyl)alumane)-5,6-dimethylbenzimidazolide, and
bis(tris(pentafluorophenyl)alumane)-5,6-bis(undecyl)benzimidazolide.

A further class of suitable activating cocatalysts include cationic Group 13 salts corresponding to the formula:

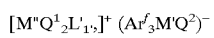

wherein:

M" is aluminum, gallium, or indium;

M' is boron or aluminum;

$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

l' is a number greater than zero indicating the number of Lewis base moieties, L', and $Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris(fluoroaryl)borates corresponding to the formula: $[M"Q^1{}_2L'_{l'}]^+ (Ar^f{}_3BQ^2)^-$, wherein M" is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl)borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefins compounds, including ethylidene norbornene, 1,4-hexadiene, norbornadiene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from $1:10^6$ to $1:10^3$, more preferably from $1:10^6$ to $1:10^4$.

In most polymerization reactions the molar ratio of catalyst:polymerizable compounds employed is from $10^{-12}:1$ to $10^{-1}:1$, more preferably from $10^{-9}:1$ to $10^{-5}:1$.

Suitable solvents use for solution polymerization are liquids that are substantially inert under process conditions encountered in their usage. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In a preferred embodiment, a heterogeneous catalyst is prepared by reacting an inorganic compound, preferably a tri($C_{1-4}$ alkyl)aluminum compound, with an activating cocatalyst, especially an ammonium salt of a hydroxyaryl(trispentafluorophenyl)borate, such as an ammonium salt of (4-hydroxy-3,5-ditertiarybutylphenyl)tris(pentafluorophenyl)borate or (4-hydroxyphenyl)tris(pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise, the α-olefin monomer or a mixture of different α-olefin monomers may be used in whole or part as the diluent. Most preferably, at least a major part of the diluent comprises the (x-olefin monomer or monomers to be polymerized. A dispersant, particularly an elastomer, may be dissolved in the diluent utilizing techniques known in the art, if desired.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas, such as, for example, nitrogen.

The polymerization may be carried out as a batchwise or a continuous polymerization process. A continuous process is preferred, in which event catalyst, ethylene, comonomer, and optionally solvent, are continuously supplied to the reaction zone, and polymer product continuously removed therefrom.

Without limiting in any way the scope of the invention, one means for carrying out such a polymerization process is as follows: In a stirred-tank reactor, the monomers to be polymerized are introduced continuously, together with solvent and an optional chain transfer agent. The reactor contains a liquid phase composed substantially of monomers, together with any solvent or additional diluent and dissolved polymer. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours.

Ethylene homopolymers and ethylene/α-olefin copolymers are particularly suited for preparation according to the invention. Generally such polymers have densities from 0.85 to 0.96 g/ml. Typically the molar ratio of α-olefin comonomer to ethylene used in the polymerization may be varied in order to adjust the density of the resulting polymer. When producing materials with a density range of from 0.91 to 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than about 0.5, preferably less than 0.2, more preferably less than 0.05, even more preferably less than 0.02 and may even be less than 0.01.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc.

All solvents were purified using the technique disclosed by Pangborn et al, *Organometallics,* 15, 1518–1520, (1996). $^1$H and $^{13}$C NMR shifts were referenced to internal solvent resonances and are reported relative to TMS.

Example 1

1,8-dihydro-3-hydoxy-dibenzo[e,h]azulene (keto isomer)

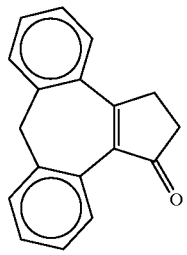

(A) Preparation of 10-(trimethylsilyl)ethynyl-5H-dibenzo[a,d]cycloheptene

To a stirred mixture of 10-bromo-5H-dibenzo[a,d] cycloheptene (9.70 g, 0.036 mol) (*J. Med. Chem.* 1995 38(4), 708–714), palladium(II)chloride bistriphenylphosphine (1.25 g, 0.018 mol), triphenyl phosphine (0.942 g, 0.0036 mol), copper(ll)acetate hydrate (0.327 g, 0.002 mol) in 20 ml of diisopropyl amine was added (trimethylsilyl)acetylene (3.88 g, 0.040 mol) and refluxed for an hour. The resulting mixture was concentrated, diluted with hexane (25 ml) and filtered through a pad of silica gel. The filtrate was concentrated to yield 5.57 g of 10-(trimethylsilyl)ethynyl-5H-dibenzo[a,d]cycloheptene.

(B) Preparation of 1,8-dihydro-3-hydoxy-dibenzo[e,h]azulene

A mixture of 10-(trimethylsilyl)ethynyl-5H-dibenzo[a,d] cycloheptene (5.57 g, 0.020 mol), triethyl amine(3.89 g, 0.039 mol), water (3.45 g, 0.385 mol), tristriphenyl phosphine rhodium chloride (0.178 g, 0.002 mol) and triphenyl phosphine (2.52 g, 0.010 mol) in 70 ml of THF was pressurized in a Parr reactor with carbon monoxide to 800 psi (690 kPa) and stirred and heated to 160C for 10 hr. The product, 1,8-dihydro-3-hydoxy-dibenzo[e,h]azulene, was isolated by concentrating the reaction and chromatography of the residue over silica gel with methlyene chloride as eluant to give 3.39 g of yellow oil.

$^1$H NMR ($C_6D_6$, 300 MHz; δ (ppm): 2.8 (m), 3.0 (br,d), 3.45 (b,d), 3.6 (br,d), 3.85 (br,d), 7,35 (m), 7.43 (m), 7.60(d,6.5 Hz), 7.91(d,6.5 Hz).

$^{13}$C NMR ($C_6D_6$, 75.45 MHz; δ (ppm)): 28.1, 34.7, 41.2, 125.8, 126.1, 127.3, 128.2, 128.9, 129.5, 131.2, 133.9, 138.9, 140.3, 167.5, 207.1

IR: C=O 1697 cm$^{-1}$

Example 2

1,8-dihydro-dibenzo[e,h]azulene

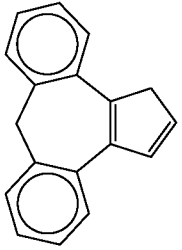

To a stirred solution of 1,8-dihydro-3hydoxy-dibenzo[e,h]azulene (3.30 g, 0.013 mol) in 50 ml of chloroform and 5 ml of ethanol was added 0.500 g (0.013 mol) of sodium borohydride and allowed to stir for 12 hr. The reaction was worked up by adding 5 ml of a 10 weight percent, aqueous HCl solution and extracting with methylene chloride. The organic layer was dried and concentrated and chromatographed over silica gel to yield 1.65 g of a white solid. The proton NMR and the mass spectrum of this material is consistent with the desired product, 1,8dihydro-dibenzo[,h]azulene.

$^1$NMR (C$_6$D$_6$, 300 MHz; δ (ppm): 3.7 (br,s), 6.6 (d,5 Hz), 7.04 (d, 5 Hz), 7.2–7.35 (m), 7.52 (d, 7 Hz)

$^{13}$C NMR (C$_6$D$_6$, 75.45 MHz; δ (ppm)): 41.9, 43.8, 126, 126.1, 126.3, 126.7, 127.8, 128.0, 132.5, 133.7, 134.7, 137.8, 137.9, 141.9, 142.1

MS (m/z): 230 (M+), 215, 202

Example 3

(2,8-dihydrodibenzo[e,h]azulen-2)-N-(1,1-dimethylethyl)dimethyl-silanamine

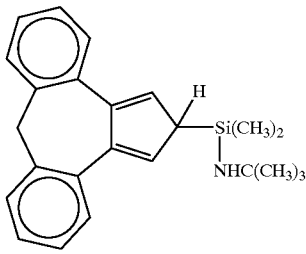

To 1,8-dihydro-dibenzo[e,h]azulene (0.461 g, 2.00 mmol) in 40 mL THF was added 2.5 M butyl lithium (0.88 mL, 2.2 mmol). The solution turned from clear colorless to dark orange immediately. After 0.5 hr. this solution was added slowly to dimethyl dichlorosilane (2.4 mL, 20 mmol) to give a pale yellow solution. Volatile materials were removed under reduced pressure. The residue was redisolved in THF and tert-butylamine (0.46 mL, 4.4 mmol) was added. A pearlescent precipitated formed within a minute. After stirring over night the volatile materials were removed under reduced pressure. The residue was extracted three times with a total of 90 mL hexanes. The extracts were filtered and volatile materials were removed from the combined filtrates under reduced pressure to give 0.716 g of a thick yellow liquid. The NMR spectra are consistent with a mixture of (2,8-dihydrodibenzo [e,h]azulen-2)-N-(1,1-dimethylethyl)dimethylsilanamine and a positional isomer (2,8-dihydrodibenzo-[e,h]azulen-1)-N-(1,1-dimethylethyl)dimethylsilanamine, as well as double bond isomers of each.

$^1$NMR (C$_6$D$_6$, 300 MHz; δ (ppm)): −0.12 (s); −0.05 (s); 0.35 (s); 0.46 (br s); 0.62 (br s); 0.94 (s); 1.11 (s); 1.13–1.21 (m); 3.51–3.85 (m); 4.18 (s); 6.61 (d, 5 Hz); 6.96–7.22 (m); 7.38 (m); 7.47 (d, 7 Hz); 7.54 (m).

$^{13}$C NMR (C$_6$D$_6$, 75.45 MHz; δ (ppm)): 0.5, 0.8, 1.8, 14.3, 33.7, 33.9, 42.3, 43.9, 47.7, 49.4, 49.6, 55.4, 126.1, 126.4, 126.5, 126.8, 127.1, 127.3, 127.6, 128.1, 128.2, 128.5, 128.8, 133.8, 134.2, 135.0, 135.2, 135.4, 138.2, 138.3, 138.5, 138.7, 141.1, 143.3, 143.8, 144.6, 146.7, 148.9.

Example 4

(2,8-dihydrodibenzo[e,h]azulen-2-yl)-N-(1,1-dimethylethyl)dimethyl-silanamide titanium dichloride

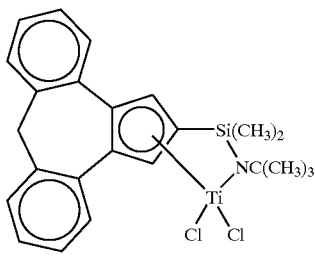

The mixture from example 3 (0.716 g, 1.99 mmol) was dissolved in 40 mL n-octane and titanium tetrakis (dimethylamide) (0.446 g, 1.99 mmol) was added. The solution was heated to and stirred at reflux for 2 days. The solution turned dark red. A small aliquot of the cooled solution was removed and volatile components of this aliquot were removed under reduced pressure. The NMR spectra of the residue are consistent with (2,8-dihydrodibenzo[e,h]azulen-2-yl)-N-(1,1-dimethylethyl)dimethyl-silanamide titanium bis(dimethylamide). Volatile materials were removed from the bulk solution under reduced pressure. The residue was dissolved in hexanes. A solution of 1.0 M boron trichloride in hexanes (4.0 mL, 4.0 mmol) was added to this solution. A precipitate formed immediately. After one hour the yellow solid was collected by vacuum filtration. The solids were washed once with hexanes. Removal of volatiles under reduced pressure gave 0.655 g of material. NMR spectra are consistent with a very pure sample of (2,8-dihydrodibenzo[e,h]azulen-2-yl)-N-(1,1-dimethylethyl)dimethyl-silanamide titanium dichloride.

$^1$NMR (C$_6$D$_6$, 300 MHz; δ (ppm)): 0.36 (S, 6H); 1.39 (s, 9H); 3.61 (d, 13.8 Hz, 1H); 4.48 (d, 13.8 Hz, 1H); 6.68 (s, 2H O; 7.02–7.16 (m, 6H); 7.43 (d, 6.6 Hz, 2H).

$^{13}$C NMR (C$_6$D$_6$, 75.45 MHz; δ (ppm)): −0.39, 32.4, 42.6, 64.1, 110.4, 123.9, 126.7, 129.1, 129.5, 130.0, 132.7, 139.7, 140.4.

Example 5

(2,8-dihydrodibenzo[e,h]azulen-2-yl)-N-(1,1-dimethylethyl)dimethyl-silanamide dimethyltitanium

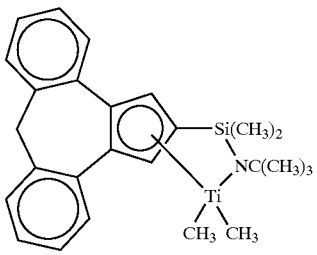

To a slurry of (2,8-dihydrodibenzo[e,h]azulen-2-yl)-N-(1,1-dimethylethyl)dimethyl-silanamide titanium dichloride (0.460 g, 0.966 mmol) in diethylether was added 3.0 M methyl magnesium chloride in THF (0.97 mL, 2.9 mmol). The color changed immediately. After stirring the mixture overnight the volatiles were removed under reduced pressure. The residue was extracted three times with a total of 90 mL hexanes. The hexanes extracts were filtered and the volatiles were removed from the combined filtrate under reduced pressure to give 0.293 g of a yellow solid. The nmr spectra are consistent with the desired compound, (2,8-dihydrodibenzo[e,h]azulen-2-yl)-N-(1,1-dimethylethyl)dimethyl-silanamide dimethyltitanium.

$^1$NMR ($C_6D_6$, 300 MHz; δ (ppm)): 0.39 (s, 6H); 0.60 (s, 6H); 1.54 (s, 9H); 3.57 (d, 13.8 Hz, 1H); 4.00 (d, 13.8 Hz, 1H); 6.31 (s, 2H); 7.08–7.2 (m, 6H); 7.59 (m, 2H).

$^{13}$C NMR ($C_6D_6$, 75.45 MHz; δ (ppm)): 0.74, 34.2, 42.5, 54.8, 59.7, 106.0, 119.9, 127.0, 128.6, 129.1, 129.2, 138.4, 134.1, 135.2.

Polymerization General Conditions

Mixed alkanes and liquid olefins are purified by sparging with purified nitrogen followed by passage through columns containing alumina (A-2, available from LaRoche Inc.) and Q5 reactant (available from Englehard Chemicals Inc.) at 50 psig using a purified nitrogen pad. All transfers of solvents and solutions described below are accomplished using a gaseous pad of dry, purified nitrogen or argon. Gaseous feeds to the reactor are purified by passage through columns of A-204 alumina (available from LaRoche Inc.) and Q5 reactant. The aluminas are previously activated by treatment at 375° C. with nitrogen, and Q5 reactant is activated by treatment at 200° C. with 5 percent hydrogen in nitrogen.

Polymerization 1

A stirred, two-liter Parr reactor was charged with approximately 433 g of toluene and 455 g of styrene comonomer. Hydrogen was added as a molecular weight control agent by differential pressure expansion from a 75 mL addition tank at 50 psig (345 kPa). The reactor was heated to 90° C. and saturated with ethylene at 200 psig (1.4 MPa). The appropriate amount of catalyst, (2,8-dihydrodibenzo-[e,h]azulen-2-yl)-N-(1,1-dimethylethyl)-dimethylsilanamide dimethyltitanium (Example 5), and cocatalyst as 0.005M solutions in toluene were premixed in a glovebox and transferred to a catalyst addition tank and injected into the reactor. (Periodic additions of catalyst/cocatalyst solution may be added during the course of the run.) The polymerization conditions were maintained during the run with ethylene on demand.

The resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos™ 168 from Ciba Geigy Corporation). Polymers formed are dried in a programmed vacuum oven with a maximum temperature of 140° C. and a 20 hour heating period. The results are contained in Table 1.

Polymerization 2

Runs 3 and 4 were performed using a 1 gallon stirred autoclave reactor. The reactor was charged with 1200 mL toluene and 400 mL styrene (run 3) or 600 mL toluene and 1000 mL styrene (run 4) then heated to the desired temperature and saturated with ethylene (1.9 MPa, 275 psig for run 3, 1.0 MPa, 150 psig for run 4). The catalyst was prepared in a drybox by mixing together the metal complex (Example 5) and cocatalyst (a mixture of dioctadecylphenylammonium tetrakispentafluorophenylborate (DPTPB) and isobutylaluminum modified methylalumoxane (Akzo Nobel MMAO-3A, 40 μmol and 70 μmol for runs 3 and 4 respectively). Additional solvent was then added to give a total volume of 13 mL.

DPTPB was prepared in the following manner. N,N-dioctadecylaniline (0.15 g, 0.25 mMol; obtained from the Sigma-Aldrich Library of Rare Chemicals) was placed into a four ounce bottle with a magnetic stir bar. Methylcyclohexane (25 mL) was added to dissolve the amine, followed by 0.125 mL of 2M HCl. The mixture was stirred vigorously for 30 minutes, then a solution of LiB($C_6F_5$)$_4$.Et$_2$O (0.191 g, 0.25 mMol; obtained from the Boulder Scientific Company) in 20 mL of water was added. The mixture was stirred for two hours. At the end of this time, a two-phase mixture was obtained; the upper (organic) layer was pale green in color. The mixture was transferred to a separatory funnel, and 30 mL of a 30 weight percent solution of NaCl in water was added. The funnel was shaken, allowed to settle, and the aqueous layer was removed and discarded. The separation was repeated with an additional 30 mL of 30 percent NaCl in water and with 30 mL of water; in each case, the aqueous layer was discarded. The organic layer that remained was dried over MgSO$_4$ for one hour, filtered, transferred to a bottle, sparged thoroughly with N$_2$, and brought into the drybox. The solution was transferred to a weighed jar, and the volatile materials were removed under vacuum. A pale green oil (0.23 g) remained. This material was dissolved in 25 mL of toluene to prepare a 0.0072M solution.

The catalyst solution was then transferred by syringe to a catalyst addition loop and injected into the reactor over approximately 1–2 minutes using a flow of high pressure solvent (toluene). The polymerization was allowed to proceed for 10 minutes while feeding ethylene on demand to maintain the reactor pressure. The amount of ethylene consumed during the reaction was monitored using a mass flow meter. The polymer solution was expelled from the reactor into a nitrogen-purged glass container containing 200 mL of isopropanol. Approximately 20 ml of a 10 weight percent toluene solution of hindered phenol antioxidant (Irganox™ 1010 from Ciba Geigy Corporation) and phosphorus stabilizer (Irgafos™ 168 from Ciba Geigy Corporation added and the solution stirred. The polymer solution was expelled into a tray, air dried overnight, then thoroughly dried in a vacuum oven for several days. Results are contained in Table 1.

TABLE 1

| Run | Cat. (μmol) | Cocatalyst (μmol) | Time (min) | T. (° C.) | Yield (g) | eff.[4] | [Styrene][5] | Mw |
|---|---|---|---|---|---|---|---|---|
| 1 | 3 | TPFB[1] (9) | 30 | 90 | 110 | 0.77 | 32.2 | — |
| 2 | 5 | DMTPB[2] (3) | 66 | 90 | 105 | 0.44 | 30.5 | — |
| 3 | 4 | DATPB[3] (4.8) | 10 | 115 | 100 | 0.52 | 12.6 | 232,000 |
| 4 | 7 | DPTPB[3] (8.4) | 10 | 90 | 146 | 0.43 | 35.6 | 120,000 |

[1] trispentafluorophenylborane
[2] dioctadecylmethylammonium tetrakispentafluorophenylborate
[3] dioctadecylphenylammonium tetrakispentafluorophenylborate (+MMAO-3A)
[4] efficiency, g polymer/μg Ti
[5] polymerized styrene content of polymer, mol percent

What is claimed is:

1. A polycyclic, fused ring compound corresponding to the formula:

$$(Cp^*)_p\text{-}M^*(I) \text{ or } CpM(Z)_z(X)_x(L)_l(X')_{x'} \quad (II),$$

where Cp* is a polycyclic, fused ring ligand or inertly substituted derivative thereof comprising at least: (1) a cyclopentadienyl ring, (2) a 6,7, or 8 membered ring other than a 6-carbon aromatic ring, and (3) an aromatic ring, with the proviso that said 6, 7, or 8 membered ring (2), is fused to both the cyclopentadienyl ring (1), and the aromatic ring (3), said Cp* having up to 60 atoms other than hydrogen;

p is 1 or 2;

when p is 1, M* is an alkali metal or an alkaline earth metal halide, and, when p is 2, M* is an alkaline earth metal; said M* being bound to at least one of the non-fused, ring-carbons of the cyclopentadienyl ring, (1);

Cp is the aromatic ligand group derived from Cp* by removal of M*;

M is a metal selected from Groups 3–10 or the Lanthanide series of the Periodic Table of the Elements;

Z is either:
   a) a cyclic ligand group containing delocalized π-electrons, including a second or third, fused, polycyclic ligand, Cp, said Z being bonded to M by means of delocalized π-electrons and optionally also covalently bonded to Cp through a divalent bridging group, Z', or
   b) a divalent moiety of the formula —Z'Y—, wherein, Z' is $SiR^6_2$, $CR^6_2$, $SiR^6_2SiR^6_2$, $CR^6_2CR^6_2$, $CR^6CR^6$, $CR^6_2SiR^6_2$, $BR^6$, $BR^6L''$, or $GeR^6_2$;
   Y is —O—, —S—, —NR$^5$—, —PR$^5$—; —NR$^5_2$, or —PR$^5_2$;
   $R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;
   $R^6$, independently each occurrence, is hydrogen, or a member selected from hydrocarbyl, hydrocarbyloxy, silyl, halogenated alkyl, halogenated aryl, —NR$^5_2$, and combinations thereof, said $R^6$ having up to 20 non-hydrogen atoms, and optionally, two groups form a ring system;
   L'' is a monodentate or polydentate Lewis base optionally bonded to $R^6$;
X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a diavalent anionic ligand group having up to 60 atoms other than hydrogen;

z is 0, 1 or 2;

x is 0, 1, 2, or 3;

l is a number from 0 to 2; and x' is 0 or 1.

2. A compound or complex according to claim 1 corresponding to the formula:

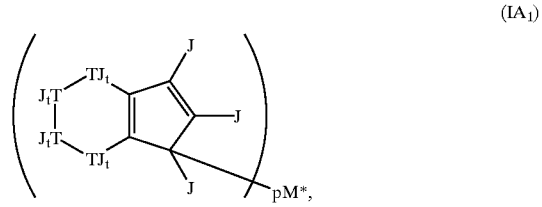

(IA₁)

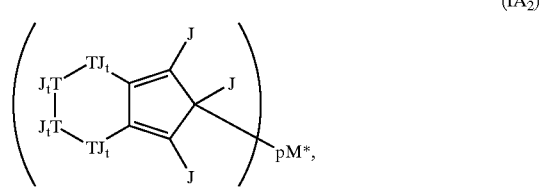

(IA₂)

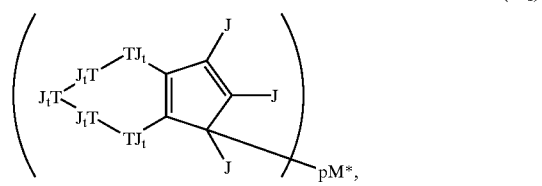

(IB₁)

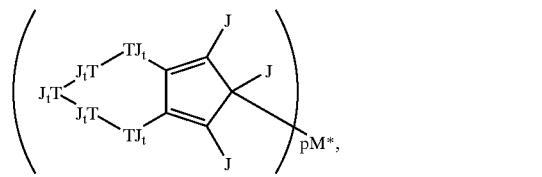

(IB₂)

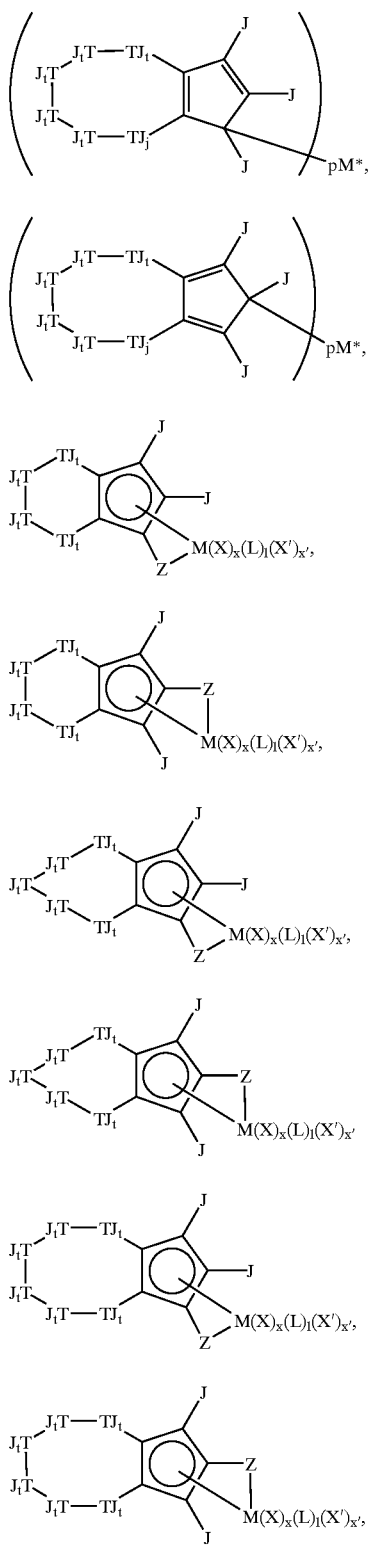

structural isomers thereof wherein one or more double bonds occupy different positions within the various rings, and mixtures thereof, wherein:

T independently each occurrence is carbon, silicon, nitrogen, phosphorus, oxygen, sulfur, or boron;

J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and optionally two J groups together form a divalent derivative thereby forming a saturated or unsaturated ring, with the proviso that, in at least one occurrence, two or more of the foregoing J groups on different atoms, at least one or which is T, together form a divalent derivative, thereby forming at least one aromatic ring that is fused to the 6, 7, or 8 membered ring;

t is 0, 1 or 2; and, for compounds of formula ($1A_1$) or ($1A_2$) where T is carbon, in at least one occurrence, t is 2; and M*, p, M, Z, X, L, X', x, l, and x' are as previously defined in claim 1.

3. A metal complex according to claim 1, corresponding to the formula:

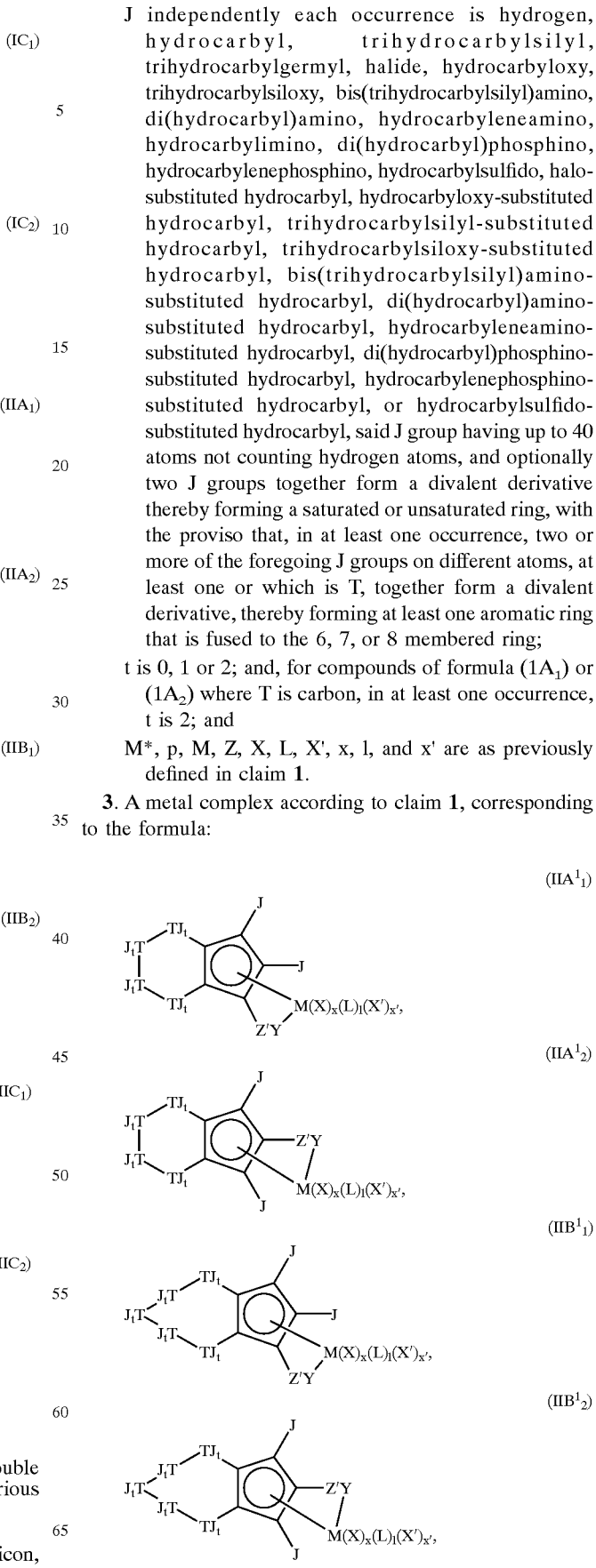

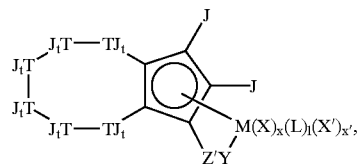
(IIC¹₁)

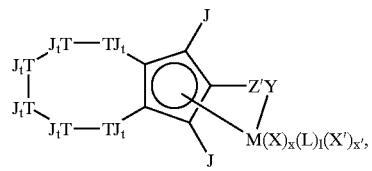
(IIC¹₂)

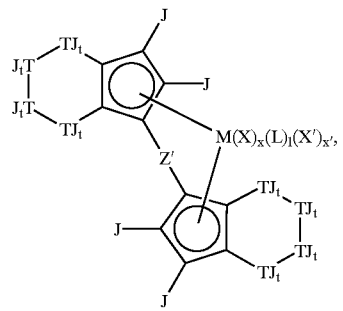
(IIA²₃)

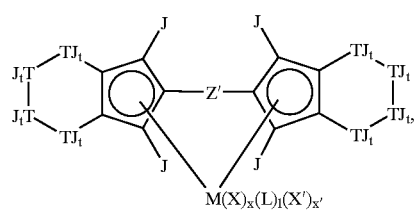
(IIA²₄)

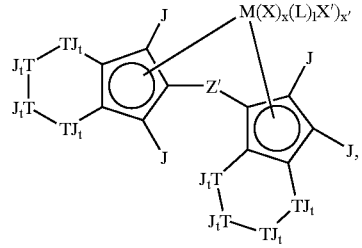
(IIA²₅)

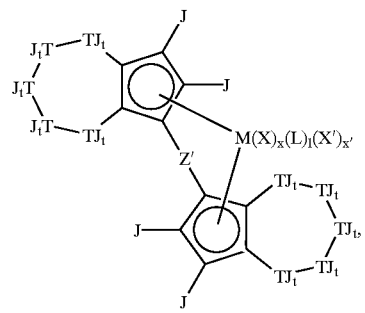
(IIB²₃)

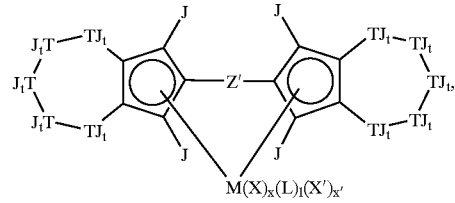
(IIB²₄)

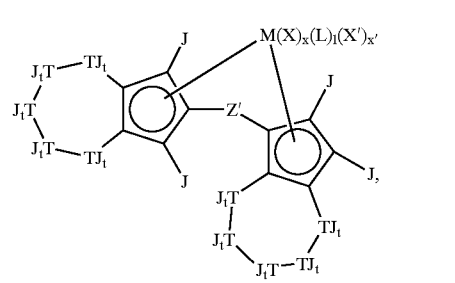
(IIB²₅)

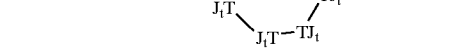
(IIC²₃)

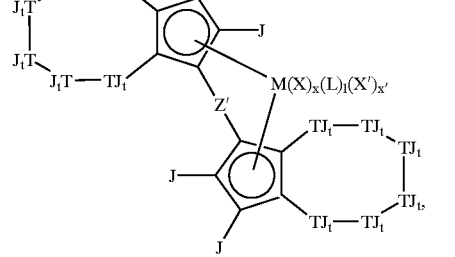
(IIC²₄)

(IIC²₅)

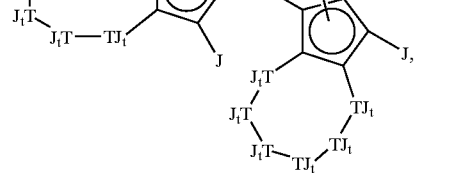

structural isomers thereof wherein one or more double bonds occupy different positions within the various rings, or a mixture thereof, wherein:
T independently each occurrence is carbon, silicon, nitrogen, phosphorus, oxygen, sulfur, or boron;
J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and optionally two J groups together form a divalent derivative thereby forming a saturated or unsaturated ring, with the proviso that, in at least one occurrence, two or more of the foregoing J groups on different atoms, at least one or which is T, together form a divalent derivative, thereby forming at least one aromatic ring that is fused to the 6, 7, or 8 membered ring;

t is 0, 1 or 2; and, for compounds of formula (1A$_1$) or (1A$_2$) where T is carbon, in at least one occurrence, t is 2; and M, Z', X, L, X', x, l, and x' are as previously defined in claim 1.

4. A compound or complex according to claim 1, corresponding to the formula:

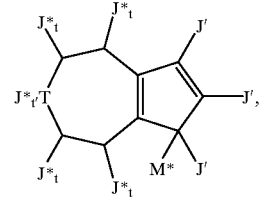
(IB$^a_1$)

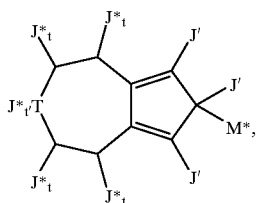
(IB$^a_2$)

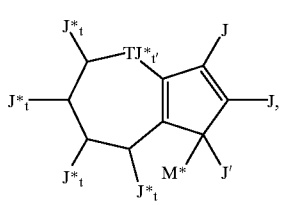
(IB$^b_1$)

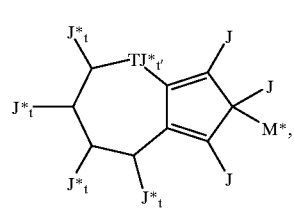
(IB$^b_2$)

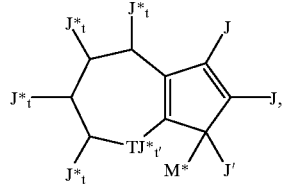
(IB$^{b'}_1$)

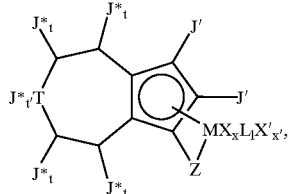
(IIB$^a_1$)

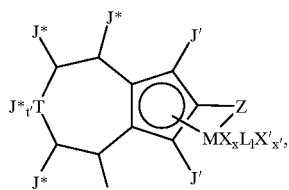
(IIB$^a_2$)

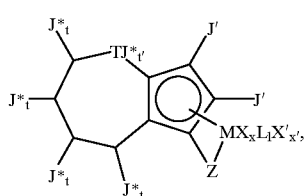
(IIB$^b_1$)

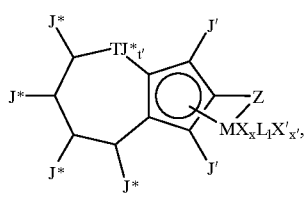
(IIB$^b_2$)

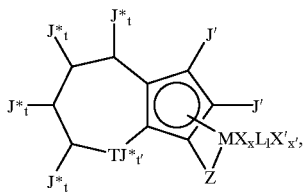
(IIB$^{b'}_1$)

structural isomers thereof wherein one or more double bonds occupy different positions within the various rings, and mixtures thereof, wherein J* independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis (trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino substituted hydrocarbyl, hydrocarbylenephosphino-substituted hydrocarbyl, or hydrocarbylsulfido-substituted hydrocarbyl, said J* group having up to 40 atoms not counting hydrogen atoms, and two J* groups together or a J* and a J' group together may form a divalent derivative thereby forming a saturated or unsaturated ring, with the proviso that, in at least one occurrence, two or more of the foregoing J* groups on different atoms, together form a divalent derivative, thereby forming at least one aromatic ring that is fused to the 6, 7, or 8 membered ring;

J' independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J' group having up to 40 atoms not counting hydrogen atoms, and two J' groups together or a J' group and a J* group together may form a divalent derivative thereby forming a saturated or unsaturated fused ring;

M* is hydrogen, an alkali metal or an alkaline earth metal halide,

T is carbon, boron, nitrogen or oxygen, t is 1 or 2;

t' is 0, 1 or 2, and

M, X, L, X', x, l, and x' are as defined in claim 3.

5. A metal compound or complex according to claim 4 corresponding to the formula:

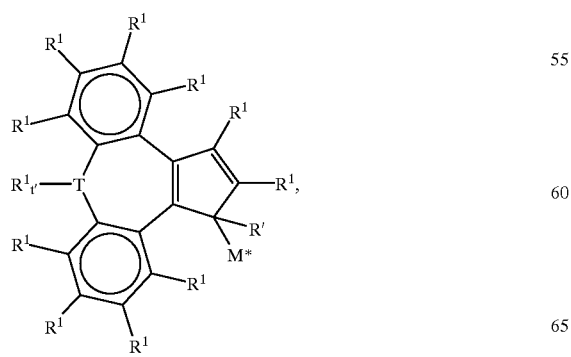

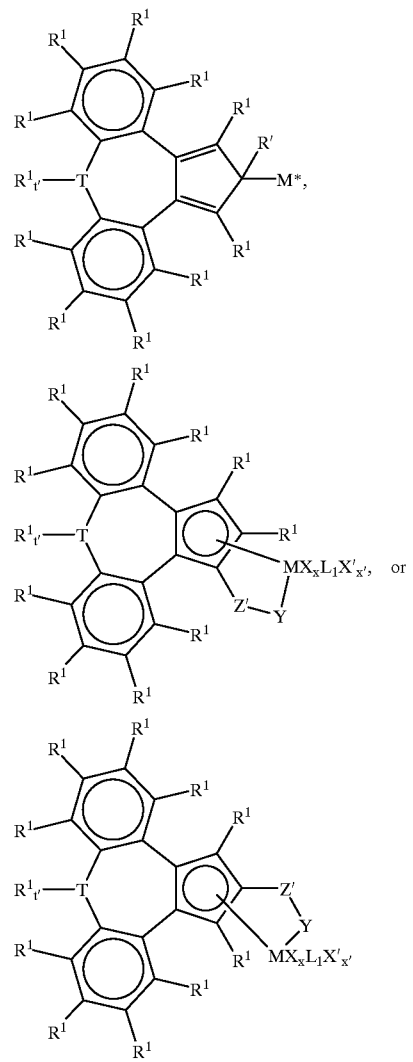

wherein
T is carbon, or nitrogen;
when T is carbon, t' is 2, and when T is nitrogen, t' is 1;
M* is hydrogen, sodium, potassium, or lithium;
M is titanium;
$R^1$ each occurrence is hydrogen or a hydrocarbyl, amino or amino-substituted hydrocarbyl group of up to 20 atoms other than hydrogen, and optionally two R' groups may be joined together;
Y is —O—, —S—, —$NR^5$-, —$PR^5$-; —$NR^5_2$, or —$PR^5_2$;
Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;
$R^5$ each occurrence is independently hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;
$R^6$ each occurrence is independently hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;

X, L, L",and X' are as previously defined;

x is 0, 1 or 2;

l is 0 or 1; and x' is 0 or 1;

with the proviso that:

when x is 2, X' is zero, M is in the +4 formal oxidation state (or M is in the +3 formal oxidation state if Y is —$NR^5_2$ or —$PR^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and X' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and X' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when x and X' are both 0, l is 1, M is in the +2 formal oxidation state, and L is a neutral, conjugated or nonconjugated diene, optionally substituted with one or more hydrocarbyl groups, said L having up to 40 carbon atoms and being bound to M by means of delocalized π-electrons thereof.

6. A metal complex according to claim 1 that is:

(2,8-dihydrodibenzo[e,h]azulen-2-yl)-N-(1,1-dimethylethyl)dimethyl-silanamide titanium (II) 1,4-diphenyl-1,3-butadiene, (2,8-dihydrodibenzo[e,h]azulen-2-yl)-N-(1,1-dimethylethyl)dimethyl-silanamide titanium (II) 1,3-pentadiene, ((2,8-dihydrodibenzo[e,h]azulen-2-yl)-N-(1,1-dimethylethyl)dimethyl-silanamide titanium (III) 2-(N,N-dimethylamino)benzyl, (2,8-dihydrodibenzo[e,h]azulen-2-yl)-N-(1,1-dimethylethyl)dimethyl-silanamide titanium (IV) dichloride, 2,8-dihydrodibenzo[e,h]azulen-2-yl)-N-(1,1-dimethylethyl)dimethyl-silanamide titanium (IV) dimethyl, 2,8-dihydrodibenzo[e,h]azulen-2-yl)-N-(1,1-dimethylethyl)dimethyl-silanamide titanium (IV) dibenzyl, (2,8-dihydrodibenzo [e,h]azulen-2-yl)-N-(cyclohexyl)dimethyl-silanamide titanium (II) 1,4-diphenyl-1,3-butadiene, (2,8-dihydrodibenzo[e,h]azulen-2-yl)-N-(cyclohexyl)dimethyl-silanamide titanium (II) 1,3-pentadiene, ((2,8-dihydrodibenzo[e,h]azulen-2-yl)-N-(cyclohexyl)dimethyl-silanamide titanium (III) 2-(N,N-dimethylamino)benzyl, (2,8-dihydrodibenzo[e,h]azulen-2-yl)-N-(cyclohexyl)dimethyl-silanamide titanium (IV) dichloride, 2,8-dihydrodibenzo[e,h]azulen-2-yl)-N-(cyclohexyl)dimethyl-silanamide titanium (IV) dimethyl, 2,8-dihydrodibenzo[e,h]azulen-2-yl)-N-(cyclohexyl)dimethyl-silanamide titanium (IV) dibenzyl, (2,8-dihydrodibenzo [e,h]azulen-1-yl)-N-(1,1-dimethylethyl)dimethyl-silanamide titanium (II) 1,4-diphenyl-1,3-butadiene, (2,8-dihydrodibenzo[e,h]azulen-1-yl)-N-(1,1-dimethylethyl)dimethyl-silanamide titanium (II) 1,3-pentadiene, ((2,8-dihydrodibenzo [e,h]azulen-1-yl)-N-(1,1-dimethylethyl)dimethyl-silanamide titanium (III) 2-(N,N-dimethylamino)benzyl, (2,8-dihydrodibenzo[e,h]azulen-1-yl)-N-(1,1-dimethylethyl)dimethyl-silanamide titanium (IV) dichloride, 2,8-dihydrodibenzo[e,h]azulen-1-yl)-N-(1,1-dimethylethyl)dimethyl-silanamide titanium (IV) dimethyl, 2,8-dihydrodibenzo[e,h]azulen-1-yl)-N-(1,1-dimethylethyl)dimethyl-silanamide titanium (IV) dibenzyl, (2,8-dihydrodibenzo[e,h]azulen-1-yl)-N-(cyclohexyl)dimethyl-silanamide titanium (II) 1,4-diphenyl-1,3-butadiene, (2,8-dihydrodibenzo[e,h]azulen-1-yl)-N-(cyclohexyl)dimethyl-silanamide titanium (II) 1,3-pentadiene, ((2,8-dihydrodibenzo[e,h]azulen-1-yl)-N-(cyclohexyl)dimethyl-silanamide titanium (III) 2-(N,N-dimethylamino)benzyl, (2,8-dihydrodibenzo[e,h]azulen-1-yl)-N-(cyclohexyl)dimethyl-silanamide titanium (IV) dichloride, 2,8-dihydrodibenzo[e,h]azulen-1-yl)-N-(cyclohexyl)dimethyl-silanamide titanium (IV) dimethyl, 2,8-dihydrodibenzo[e,h]azulen-1-yl)-N-(cyclohexyl)dimethyl-silanamide titanium (IV) dibenzyl, or a mixture thereof.

* * * * *